US012594029B2

(12) United States Patent
Rea et al.

(10) Patent No.: US 12,594,029 B2
(45) Date of Patent: Apr. 7, 2026

(54) IMPLANT STABILITY SENSOR SYSTEM AND METHOD

(71) Applicant: OrthoIQ, LLC, Claremont, CA (US)

(72) Inventors: Donald Eugene Rea, Claremont, CA (US); Phillip Ormond Merritt, La Canada, CA (US); Sahil Kashyap, Landing, NJ (US); Alan Aaron Davidner, Claremont, CA (US); Randall Carl Danta, Georgetown, TX (US); Kimberly Elasky, Westlake Village, CA (US)

(73) Assignee: OrthoIQ, LLC, Claremont, CA (US)

( * ) Notice: Subject to any disclaimer, the term of this patent is extended or adjusted under 35 U.S.C. 154(b) by 0 days.

(21) Appl. No.: 18/790,455

(22) Filed: Jul. 31, 2024

(65) Prior Publication Data

US 2025/0040882 A1 Feb. 6, 2025

Related U.S. Application Data

(60) Provisional application No. 63/516,665, filed on Jul. 31, 2023.

(51) Int. Cl.
| | |
|---|---|
| *A61B 5/00* | (2006.01) |
| *A61B 1/317* | (2006.01) |
| *A61B 34/20* | (2016.01) |
| *A61B 90/00* | (2016.01) |
| *A61F 2/46* | (2006.01) |

(52) U.S. Cl.
CPC ............ *A61B 5/4851* (2013.01); *A61B 1/317* (2013.01); *A61B 5/4884* (2013.01); *A61B 5/686* (2013.01); *A61B 34/20* (2016.02); *A61F 2/4657* (2013.01); *A61B 2034/2055* (2016.02); *A61B 2034/2065* (2016.02); *A61B 2090/3916* (2016.02); *A61B 2090/3937* (2016.02); *A61F 2002/4633* (2013.01); *A61F 2002/4666* (2013.01)

(58) Field of Classification Search
CPC .... A61B 2090/3916; A61B 2090/3937; A61B 5/4851; A61B 2034/2055; A61B 2034/2057; A61B 2034/2065; A61F 2/4657; A61F 2002/4666
See application file for complete search history.

(56) References Cited

U.S. PATENT DOCUMENTS

| | | | |
|---|---|---|---|
| 6,370,418 B1 * | 4/2002 | Bernoski | ................. A61F 2/468 600/426 |
| 2011/0054625 A1 | 3/2011 | Ferko et al. | |

(Continued)

OTHER PUBLICATIONS

International Search Report dated Oct. 28, 2024 re PCT/US2024/040187 (3 pages).

(Continued)

*Primary Examiner* — Angela M Hoffa
(74) *Attorney, Agent, or Firm* — Aurora Consulting LLC; Albert Du; Ashley Sloat

(57) ABSTRACT

A system for detecting motion between an implant and a bone that can optionally include: a bone locator means configured to be coupled to the bone, an implant attachment means configured to be coupled to the implant, and a data analysis means. The implant attachment means includes a detection means, and the implant attachment means defines one or more apertures or surfaces for receiving a force from a force inducing means.

20 Claims, 20 Drawing Sheets

(56) References Cited

U.S. PATENT DOCUMENTS

| | | | | |
|---|---|---|---|---|
| 2013/0338492 A1* | 12/2013 | Munro | ................. | A61B 6/5229 |
| | | | | 600/424 |
| 2016/0089079 A1* | 3/2016 | Stein | ................... | A61B 5/0008 |
| | | | | 600/300 |
| 2016/0310066 A1* | 10/2016 | Wiedenhoefer | ...... | G01C 22/006 |
| 2017/0164962 A1 | 6/2017 | Olson | | |
| 2017/0262595 A1 | 9/2017 | Vorhis et al. | | |
| 2020/0022744 A1 | 1/2020 | Behzadi | | |
| 2021/0186454 A1* | 6/2021 | Behzadi | ................. | A61B 7/023 |
| 2022/0331009 A1 | 10/2022 | Nevins et al. | | |
| 2025/0072828 A1* | 3/2025 | Meyer | ................... | G16H 10/60 |

OTHER PUBLICATIONS

Taylor, Mark et al. article titled "Influence of Loading and Activity on the Primary Stability of Cementless Tibial Trays," Journal of Orthopaedic Research Sep. 2012 , accepted Dec. 6, 2011, Published online Jan. 20, 2012 in Wiley Online Library (wileyonlinelibrary. com) DOI 10.1002/jor.22056 (7 pages).

Townsend, Katy article titled The Use of Radiographs, Dual-energy X-ray Absorptiometry, Quantitative Computed Tomography and Micro-computed Tomography to Determine Local Cancellous Bone Quality in the Canine Proximal Femur, Dec. 31, 2012 (Dec. 31, 2012) [retrieved on Oct. 15, 2024]. Retrieved from the internet entire document (49 pages).

Written Opinion dated Oct. 28, 2024 re PCT/US2024/040187 (26 pages).

* cited by examiner

100

Implant Stability Sensor

| | |
|---|---|
| Bone Locator 110 | Motion Detector 140 |
| Implant Attachment 120 | Data Analyzer 150 |
| Force Inducer 130 | User Interface 160 |

200

501

510

910

970

930

960

1100

Affix a marking pin to a bone
S1110

Affix a motion detector to an implant
S1120

Induce forces on the implant relative to the bone
S1130

Detect implant motion relative to the bone
S1140

Output an indication of implant stability
S1150

1200

S1210

Affix a marking pin to a bone

S1220

Affix a motion detector to an implant

S1230

Induce motion on the implant relative to the bone

S1240

Detect relative motion between the implant and the bone

S1250

Output an indication of implant movement

S1260

Output a measurement of implant stability

1300

S1310

Affix a marking pin to a bone

S1320

Affix a motion detector to an implant

S1330

Induce motion on the implant relative to the bone

S1340

Detect relative motion between the implant and the bone

S1350

Output an indication of implant movement

S1360

Output a measurement of implant stability

S1370

Output a recommendation whether the implant should be cemented or cementless

1400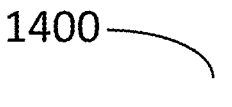

S1410

Affix a motion detector to a bone

S1420

Affix a strike pad to an implant

S1430

Use an impactor to induce motion in the implant relative to the bone

S1440

Detect relative motion between the implant and the bone

S1450

Output an indication of implant movement

S1450

Output a measurement of implant stability

S1460

Output a recommendation whether the implant should be cemented or cementless

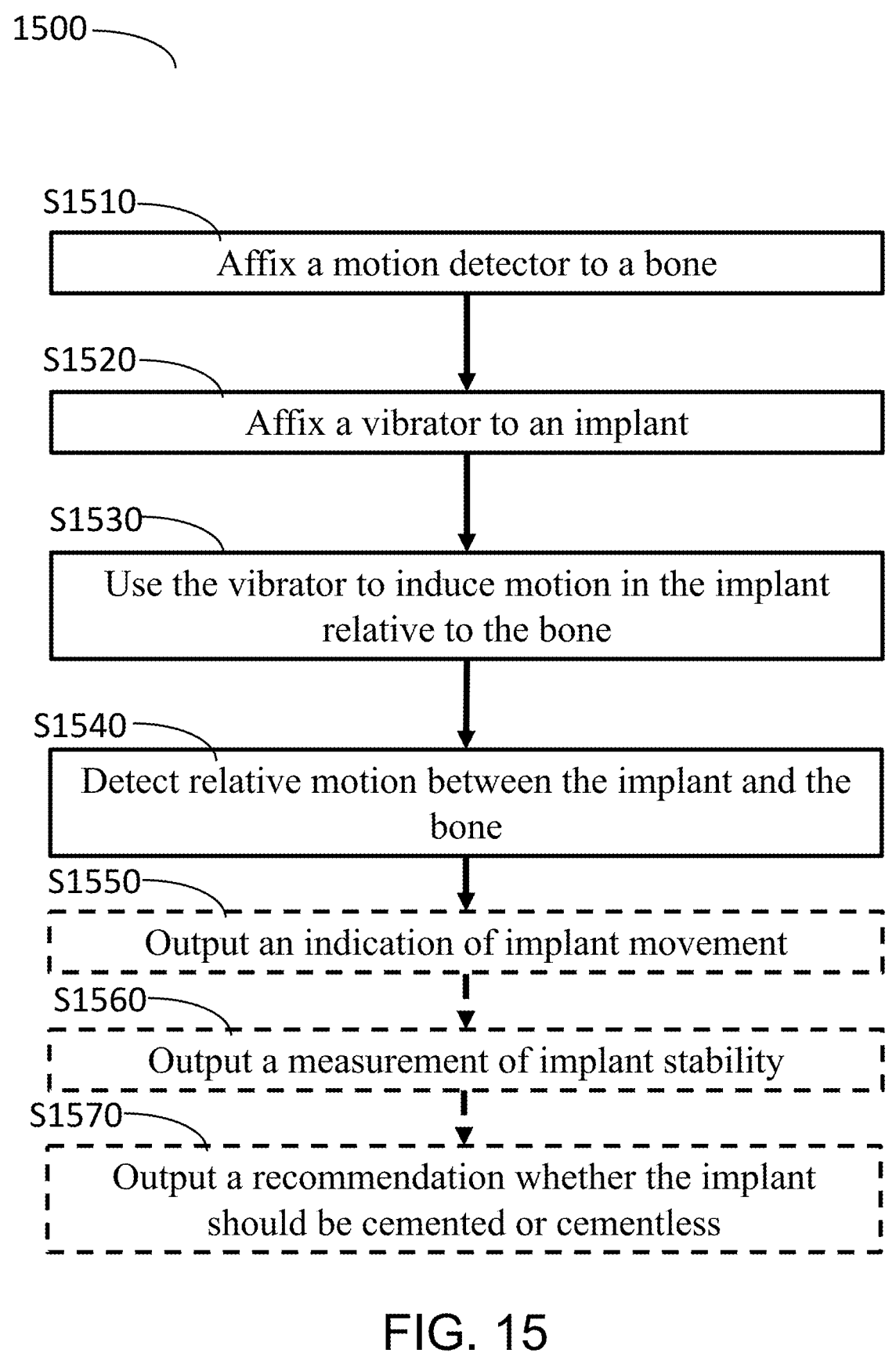

S1510 —
Affix a motion detector to a bone

S1520 —
Affix a vibrator to an implant

S1530 —
Use the vibrator to induce motion in the implant relative to the bone

S1540 —
Detect relative motion between the implant and the bone

S1550 —
Output an indication of implant movement

S1560 —
Output a measurement of implant stability

S1570 —
Output a recommendation whether the implant should be cemented or cementless

FIG. 15

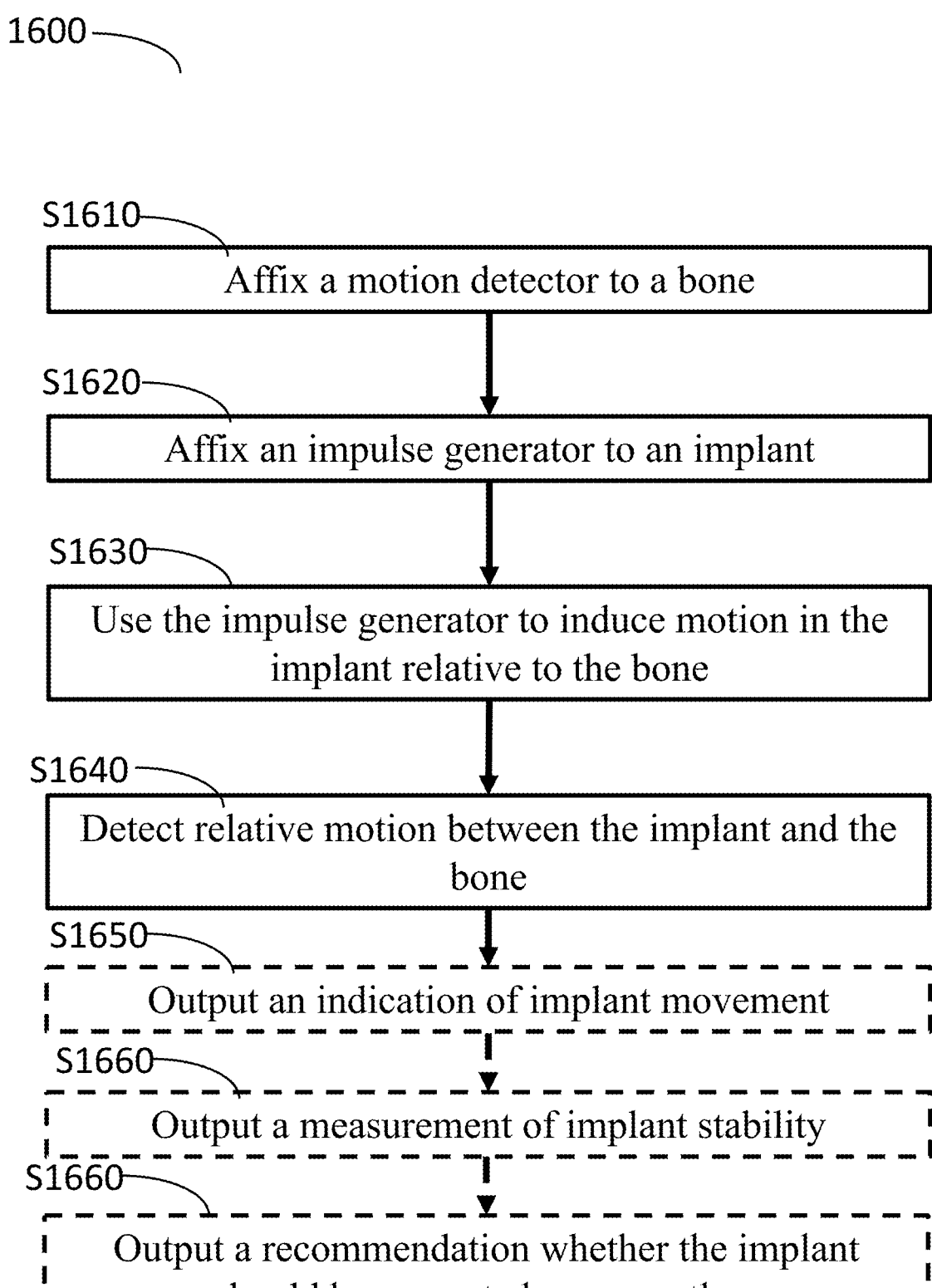

1600

S1610
Affix a motion detector to a bone

S1620
Affix an impulse generator to an implant

S1630
Use the impulse generator to induce motion in the implant relative to the bone S1640
Detect relative motion between the implant and the bone S1650
Output an indication of implant movement S1660
Output a measurement of implant stability S1660
Output a recommendation whether the implant should be cemented or cementless

FIG. 16

1700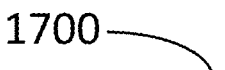

S1710

Affix a reflector to a bone

S1720

Affix a laser and photodetector to an implant

S1730

Induce motion in the implant relative to the bone

S1740

Use the laser, mirror, and photodetector to detect relative motion between the implant and the bone

S1750

Output an indication of implant movement

S1760

Output a measurement of implant stability

S1770

Output a recommendation whether the implant should be cemented or cementless

FIG. 17

1800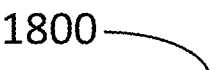

S1810

Affix a first attachment point of a strain gauge to a bone

S1820

Affix a second attachment point of a strain gauge to an implant

S1830

Induce motion in the implant relative to the bone

S1840

Use the strain gauge to detect relative motion between the implant and the bone

S1850

Output an indication of implant movement

S1860

Output a measurement of implant stability

S1870

Output a recommendation whether the implant should be cemented or cementless

FIG. 18

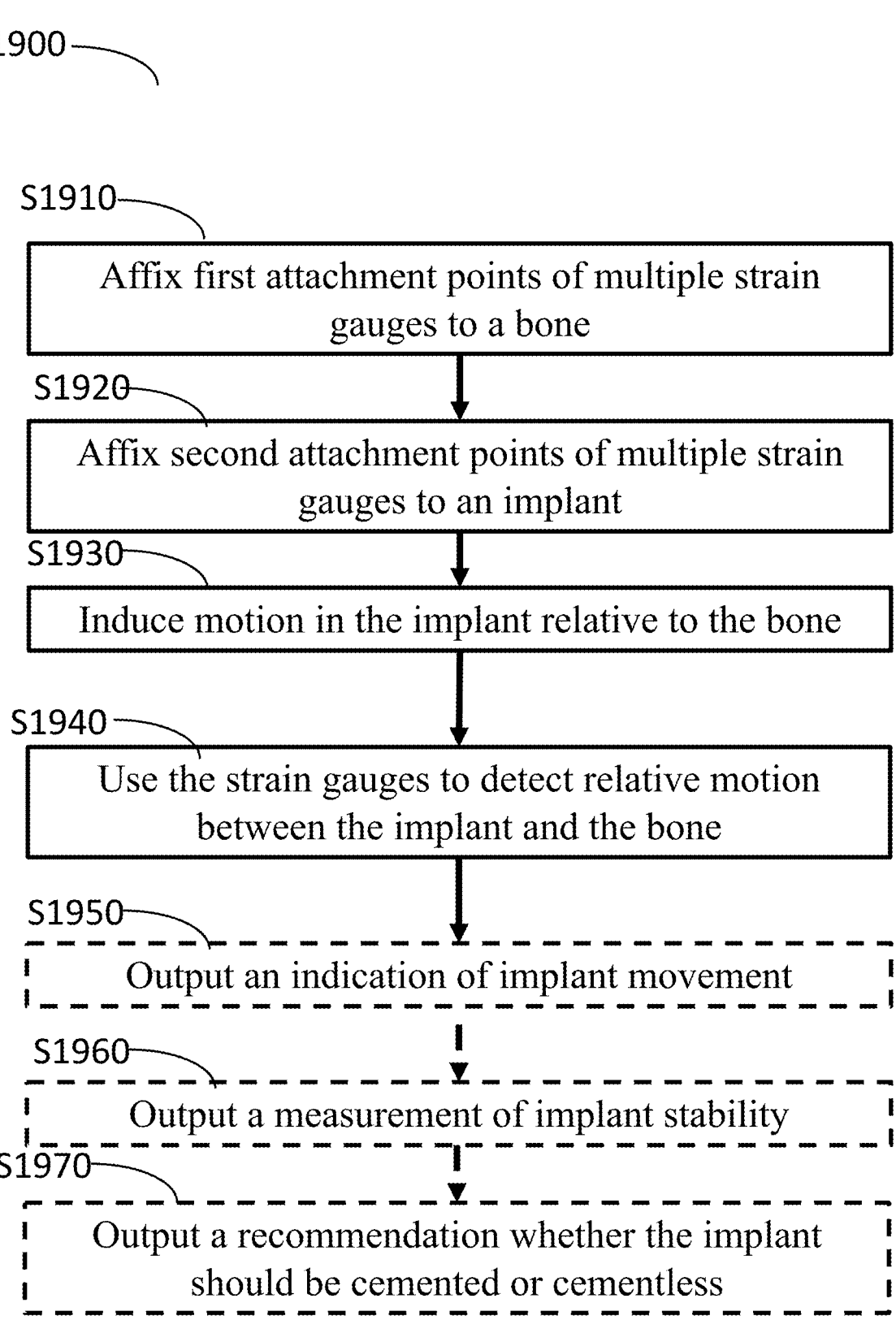

1900

S1910
Affix first attachment points of multiple strain gauges to a bone

S1920
Affix second attachment points of multiple strain gauges to an implant

S1930
Induce motion in the implant relative to the bone

S1940
Use the strain gauges to detect relative motion between the implant and the bone S1950
Output an indication of implant movement S1960
Output a measurement of implant stability S1970
Output a recommendation whether the implant should be cemented or cementless

FIG. 19

IMPLANT STABILITY SENSOR SYSTEM AND METHOD

CROSS-REFERENCE TO RELATED APPLICATIONS

This application claims the priority benefit of U.S. Provisional Patent Application Ser. No. 63/516,665, filed Jul. 31, 2023, the contents of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to implant stability measurements for orthopedic implant surgery, and more specifically to determining fit between an implant and a bone. Described herein are systems and methods for an implant stability sensor system and method.

BACKGROUND

Orthopedic implant surgery is a very common procedure for patients whose arthritis makes it difficult to perform everyday activities. During a joint replacement procedure, damaged portions of the joint are removed and replaced with prosthetic components.

Prosthetic implant surgery has become an effective, reliable, and predictable procedure to relieve pain and recover function.

Orthopedic procedures are generally associated with low morbidity and mortality, reduced joint pain, and improved range-of-motion. A number of surgical approaches is utilized with variations in device attachment technique, ligament preservation, resection, and the selection of biomaterials for manufactured components. Another variable is the use of cemented versus cementless prosthesis attachment methods.

Cemented Implants. Cemented implants are fixed into place with quick-drying bone cement that bonds the patient's natural bone with the prosthetic. Cemented implants have been used for years and are effective in the long term. The cement dries very quickly, so the implant is securely in place when the surgery is complete. On average, a cemented implant will last 10 to 20 years or more before it needs to be replaced.

Cement fixation has historically been the "gold standard" for fixation for many patients undergoing a joint replacement. For example, the majority of knee implants are cemented implants.

Over time, the bone cement that holds the implants in place can break down due to stress on the joint. Although it is uncommon for metal prosthetics to break, they can come loose from the bone if the cement begins to break down. If the implant loosens, a revision procedure may be needed. Research has highlighted that cemented joint replacements in younger patients may not last as long as those in older patients, simply due to the increased activity and demand they place on the implants and cement which may lead to premature loosening.

As the bone cement breaks down, it can leave debris behind, which can irritate the tissues surrounding the joint. This can trigger an inflammatory response within the body as it tries to remove the debris. Eventually, it can lead to a condition called osteolysis, in which the body begins to remove small bits of bone around the implant as well. Osteolysis weakens the bone, causing further loosening of the implant.

As the demand for joint replacement surgery is continuously increasing and the current age population with osteoarthritis is getting younger, cemented fixation may not provide adequate long-term outcomes due to fixation failure.

Advances in implant technology have led to implants that do not need to be cemented into place. Instead, the textured surface of the implant encourages bone growth, so the implant is rigidly fixed to the bone. Both cemented and cementless knee implants are currently used for joint replacements.

Cementless Implants. The theoretical benefits of using cementless prostheses include shorter operating room time, preservation of bone stock, case of revision, and elimination of complications associated with cemented fixation like third body wear and retained loose fragments. Osteolysis patterns also differ depending on the mode of fixation. Cementless implants, also known as press-fit implants, have a rough, porous surface that encourages new bone growth. The new bone grows into the spaces in the implant, holding it in place without the need for cement. The bones within the joint are shaped with special tools so that they fit snugly with the implant. In some cases, screws or pegs may be used to hold the prosthetics in place while the bone grows.

Because cement fixation is not needed for these types of implants, patients don't have to worry about potential complications from cement breakdown. Furthermore, studies have shown that the short-term results are comparable to that of cemented implants.

Joint replacements using a cementless implant may require a longer healing time, because it can take time for new bone growth that is sufficient enough to hold the implant in place.

Because cementless implants use the patient's natural bone to hold the implants in place, it is thought that they will last longer and form a more permanent bond with the patient's bones than cemented implants.

Generally, cementless prostheses are more expensive than cemented implants. However, accounting for cement, less operative time, and lower equipment cost, narrows the cost difference between cemented and cementless procedures.

Cementless implants are not suitable for patients who have poor bone quality due to a condition like osteoporosis. Strong, healthy bone is needed to hold the implant in place. Also, because joints take on quite a bit of stress from daily activity, microscopic debris can be created from wear on the implant. As with debris from bone cement, this can trigger an inflammatory response that leads to osteolysis.

Cementless joint replacement favors good bone quality with high metabolic activity to promote biological fixation. Indeed, a younger age (under 65 years old) and an adequate bone stock are the most typical indications.

With the development of biotechnologies and new biomaterials with high osteo-conductive properties, biological fixation is now becoming an attractive option for improving the longevity of joint implants, especially in young patients.

SUMMARY

In some aspects, the techniques described herein relate to a system for detecting motion between an implant and a bone, the system including: a bone locator means configured to be coupled to the bone; and an implant attachment means configured to be coupled to the implant, wherein: the implant attachment means includes a detection means, and the implant attachment means defines one or more apertures or surfaces for receiving a force from a force inducing means; and a data analysis means.

In some aspects, the techniques described herein relate to a computer-implemented method of measuring implant stability, the method including: receiving, from a detection means, a first image of a bone locator means affixed to a bone; determining a first location of the bone locator means in the first image; receiving, from a sensor, force signals indicative of forces induced on an implant being coupled to the bone; receiving, from the detection means, a second image of the bone locator means affixed to the bone; determining a second location of the bone locator means in the second image; determining a relative motion between the implant and the bone based on a difference between the second location and the first location; and outputting an indication of implant movement based on the determined relative motion.

In some aspects, the techniques described herein relate to a non-transitory computer-readable medium including computer-readable instructions, wherein the computer-readable instructions, when executed by a processor, cause the processor to perform operations including: receiving, from a detection means, a first image of a bone locator means affixed to a bone; determining a first location of the bone locator means in the first image; receiving, from a sensor, force signals indicative of forces induced on an implant being coupled to the bone; receiving, from the detection means, a second image of the bone locator means affixed to the bone; determining a second location of the bone locator means in the second image; determining a relative motion between the implant and the bone based on a difference between the second location and the first location; and outputting an indication of implant movement based on the determined relative motion.

In some aspects, the techniques described herein relate to a system for detecting motion between an implant and a bone, the system including: a bone locator means configured to be coupled to the bone; an implant attachment means configured to be coupled to the implant, wherein: the implant attachment means includes a detection means, and the implant attachment means defines one or more apertures or surfaces for receiving a force from a force inducing means; and a processor coupled to a memory and the detection means, wherein the memory includes computer-readable instructions stored thereon that, when executed by the processor, cause the processor to perform operations including: receiving, from the detection means, a first image of the bone locator means coupled to the bone; determining a first location of the bone locator means in the first image; receiving, from a sensor communicatively coupled to the processor, force signals indicative of forces induced on the implant being coupled to the bone; receiving, from the detection means, a second image of the bone locator means coupled to the bone; determining a second location of the bone locator means in the second image; determining a relative motion between the implant and the bone based on a difference between the second location and the first location; and outputting an indication of implant movement based on the determined relative motion.

In some aspects, the techniques described herein relate to a system for detecting motion between an implant and a bone, the system including: a bone locator configured to be coupled to the bone; an implant attachment configured to be coupled to the implant, wherein: the implant attachment includes a detector, and the implant attachment defines one or more apertures or surfaces for receiving a force from a force inducer; and a processor coupled to a memory and the detector, wherein the memory includes computer-readable instructions stored thereon that, when executed by the processor, cause the processor to perform operations including: receiving, from the detector, a first image of the bone locator coupled to the bone; determining a first location of the bone locator in the first image; receiving, from a sensor communicatively coupled to the processor, force signals indicative of forces induced on the implant being coupled to the bone; receiving, from the detector, a second image of the bone locator coupled to the bone; determining a second location of the bone locator in the second image; determining a relative motion between the implant and the bone based on a difference between the second location and the first location; and outputting an indication of implant movement based on the determined relative motion.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 14 is a flow chart of a method according to another example of the present application.

FIG. 15 is a flow chart of a method according to another example of the present application.

FIG. 16 is a flow chart of a method according to another example of the present application.

FIG. 17 is a flow chart of a method according to another example of the present application.

FIG. 18 is a flow chart of a method according to another example of the present application.

FIG. 19 is a flow chart of a method according to another example of the present application.

Figure 1:
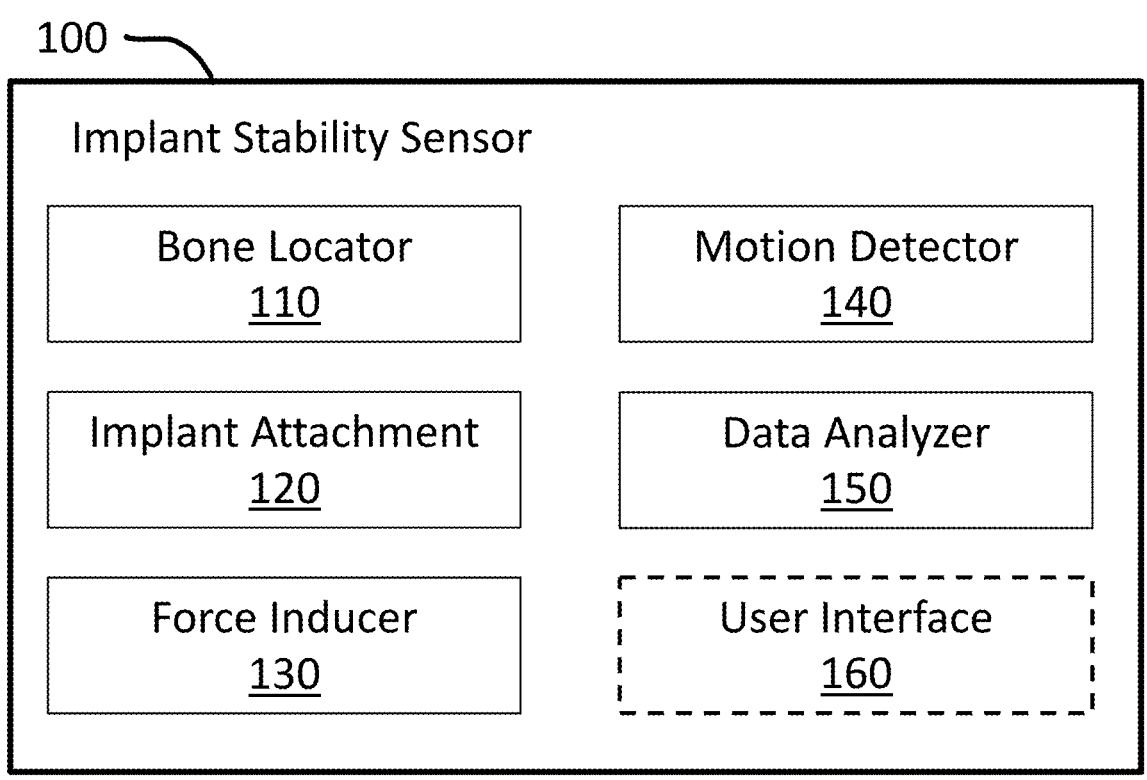
FIG. 1 is a block diagram illustrating the major electromechanical components of an exemplary implant stability sensor system, in accordance with an example of the present application.

The illustrated embodiments are merely examples and are not intended to limit the disclosure. The schematics are drawn to illustrate features and concepts and are not necessarily drawn to scale.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The disclosure pertains generally to systems of detecting implant stability and related methods. Various systems and methods for detecting relative motion between an implant and the surrounding bone are described herein. For example, during an orthopedic surgery, the physician may encounter situations of poor implant fit. In some embodiments, the technical problem is that it may be difficult to determine if the poor implant fit requires further work, qualifies for use of cement, or if the implant fit is adequate for cementless bonding methods. In some situations, it may be desirable to provide a means of determining the degree of motion between the implant and the bone as a technical solution.

To ensure stability of the implant, the bone resections should be performed accurately, and it is desirable to minimize gaps between the host bone and the implant components to reduce motion at the bone/metal interfaces. A rule of thumb is that a gap of less than about 50 microns (about 0.002 inches) is likely to support a good cementless bond.

A method of measuring implant stability is, therefore, desirable. A measurement of implant stability may measure the motion between a bone and an implant and assist a surgeon in determining whether there is a good likelihood for bone ingrowth.

Described herein are technical solutions to accomplish measurements of motion between an implant and a bone that may be used during an implant procedure for quantifying bone and implant fit. Further, systems and methods are described herein for locating a bone, attaching a motion detector to the implant, inducing forces on the implant, measuring the relative motion between the implant and the bone, and outputting a result.

In some embodiments, a further technical solution includes locating a marking pin onto a bone that remains visible during appropriate steps in a surgical procedure. In some embodiments, the marking pin may be colored or textured to remain visible to a camera and appear with adequate optical contrast against the background of surrounding bone material, flow of bodily fluids, irrigation, and/or repeated wiping to clear the surgical field. In some embodiments, the marking pin may reside outside a perimeter of the implant, so it is not covered up once the implant is set in place.

In some embodiments, a further technical solution includes providing an implant attachment to support the motion detector and facilitate inducing forces on the implant. In particular, an implant attachment is described in which a mechanical clamp engages with one or more external features or openings of an implant. In some instances, the external features or openings may be designed as part of the basic implant. In some instances, the external features or openings may be added to the implant in a cooperative effort with the implant manufacturer to facilitate use of the implant stability sensor device. In some embodiments, applying force to the implant relative to the bone may establish implant stability when the relative movement of the implant is less than about 50 microns. In some embodiments, application of a force of about 20 Newton meters or about 15 Newton meters to about 30 Newton meters can establish relative motion between the implant and the bone. The systems and methods described herein help a surgeon to determine when about 20 Nm of force has been applied by sensing the applied force with a sensor, for example in the devices described herein or in a tool used by the surgeon.

In some embodiments, a further technical solution includes estimating the gap between an implant and a bone using relative motion between the implant and bone. In some embodiments, the motion detector means can be optical, for example using a camera.

In some embodiments, a further technical solution includes inducing forces on the implant to cause motion for determining implant stability. In some embodiments, the forces may be induced by a torque wrench.

In some embodiments, a further technical solution includes analyzing images received from a camera, detecting motion, outputting a result to a user (e.g., surgeon) indicating stability of the implant, to assist the user in making an informed decision over how to proceed with the surgical procedure and specifically whether or not to use cement.

Systems and Devices

The systems and devices described herein function to measure implant stability. In some embodiments, the systems and devices function to induce forces and detect relative motion between an implant and a bone. The systems and devices are used for implant surgery, but can additionally, or alternatively, be used for any suitable applications, clinical or otherwise. The systems and devices can be configured and/or adapted to function for any suitable motion measurement. Although many of the examples and embodiments described herein are described and illustrated with respect to a Total Knee Replacement (TKA) procedure, one of skill in the art will appreciate that the examples and embodiments can be applied to hip and shoulder implants or any orthopedic surgery that includes an implant and a bone.

FIG. 1 is a simplified block diagram of various electro-mechanical components of an implant stability sensor system as disclosed herein. As shown, implant stability sensor system 100 includes bone locator 110, implant attachment 120, force inducer 130, motion detector 140, data analyzer 150, and optionally user interface 160.

Bone locator 110 can include an optical target located on or in a bone to provide a recognizable focal point for motion detector 140. In some embodiments, bone locator 110 may be intended to follow the position of the bone and remain visible to the visual field of motion detector 140 during appropriate portions of a surgical procedure. In some embodiments, bone locator 110 can include a marking pin that may reside within a drilled hole.

Implant attachment 120 can include a mechanical clamp, one or more force inducer attachment points, and one or more motion detector attachment points. The mechanical clamp may be intended to grip the implant, transfer forces to an implant, and/or follow any resulting movement of the implant. In some embodiments, the mechanical clamp may engage mechanical features of a variety of bone implants. In alternate embodiments, the mechanical clamp may include replaceable jaws adaptable to specific implant models.

In some embodiments, implant attachment 120 may include one or more force inducer attachment points that function as drive apertures capable of receiving a drive peg of force inducer 130. In some embodiments, the one or more drive apertures may substantially match the dimensions of standard square drive apertures in the range of ¼", ⅜"/or ½" across flats common to socket wrenches and other mechanical tools. In some embodiments, the one or more drive apertures can be positioned at specific locations disposed about implant attachment 120. In some embodiments, each drive aperture includes a specific axis of rotation. In some embodiments, the one or more drive apertures may include an axis of rotation arranged in orthogonal X-Y-Z directions relative to the implant. Axis of rotation of the one or more drive apertures may be arranged in other angular directions to suit the needs of the specific joint replacement surgery.

Force inducer 130 can be a tool intended to manually impart forces to the one or more drive apertures of implant attachment 120, and, by virtue of their clamped engagement, subsequently transfer forces to the implant. In some embodiments, force inducer 130 can include a torque wrench with one or more drive pegs that may substantially match the dimensions of standard square drive pegs in the range of ¼", ⅜"/or ½" across flats common to socket wrenches and other mechanical tools. In some embodiments, the one or more drive pegs of force inducer 130 are configured to be removably engaged with one or more drive apertures of implant attachment 120. Manual forces applied to the hand grip of the torque wrench result in torsional forces upon implant attachment 120.

In some embodiments, force inducer 130 can be an electronic torque wrench capable of having a pre-set torque value programmed into its memory. In some embodiments, a visual or audible signal may be produced by the torque wrench capable of notifying a user that a pre-set torque value has been reached. In other embodiments, a radio signal may be produced by the torque wrench including the current torque value and also indicating when a pre-set torque value has been reached. In some embodiments, the radio signal is a wireless signal (e.g., Bluetooth, Wi-Fi, etc.) that can be transmitted to the motion detector 140 including the current torque value and also indicating when a pre-set torque value has been reached. In other embodiments, the force inducer 130 can be a lever, breaker bar, impactor, vibrator, or impulse generator. In some embodiments, the force inducer 130 is configured to induce the force on the implant in a variety of directions relative to the bone, including but not limited to a direction axial, transverse vertical, transverse horizontal, or rotational relative to the bone.

Motion detector 140 may be a machine vision device intended to detect relative motion between itself and bone locator 110 and provide data analyzer 150 with information indicating the relative position and movement of bone locator 110 within the field of view of motion detector 140.

In some embodiments, motion detector 140 may include a camera and means for attaching the camera to implant attachment 120. In some embodiments, the camera may operate to recognize the position of bone locator 110, and transfer images to motion detector 140. In some embodiments, images can include a substantially circular contrasting spot indicating the current location of bone locator 110 within the field of view of motion detector 140. In some embodiments, the camera can produce a sequence of images with the contrasting spot represented as a locus of points indicating position of bone locator 110 at various time intervals.

In some embodiments, the camera may have an external lens. In some embodiments, the camera lens may allow for adjustments to field of view and/or focal length. In some embodiments, the camera lens may minimize optical aberrations. In some embodiments, the camera lens can be aspheric.

In some embodiments, motion detector 140 may be mechanically fixed to implant attachment 120. In some embodiments, motion detector 140 may be removably attached to implant attachment 120.

In some embodiments, motion detector 140 can be electrically hard-wired to data analyzer 150. In other embodiments, a radio signal is produced by motion detector 140 and transmitted to data analyzer 150. In some embodiments, the radio signal may include Bluetooth, Near-Field communication, other radiofrequency communication, LTE, 5G, Zigbee, and the like.

Data analyzer 150 may be an electronic subsystem configured to receive signals from motion detector 140, analyze signals to determine implant stability, optionally output a determination of implant stability, and optionally communicate results to a user via optional user interface 160. In some embodiments, data analyzer 150 can include a processor configured to execute computer-readable instructions stored on a memory, as described in FIG. 2. In some embodiments, the computer-readable instructions are stored on a non-transitory computer-readable medium.

Optional user interface 160 can be a visual or auditory component for notifying a user of a result output from data analyzer 150. In some embodiments, optional user interface 160 can produce sound patterns to indicate various status and/or outcomes. For example, a beep may indicate that force inducer 130 has reached a pre-set torque value. In other examples, sounds may indicate poor implant fit requiring more work, good implant fit suitable for cement, or superior implant fit suitable for a cementless implant. In some embodiments, optional user interface 160 can produce visual patterns, including text, graphics, or video clips to indicate various status and/or outcomes. In some embodiments, an Artificial Intelligence (AI) interface may be included to conduct verbal dialog with the user.

Figure 2:
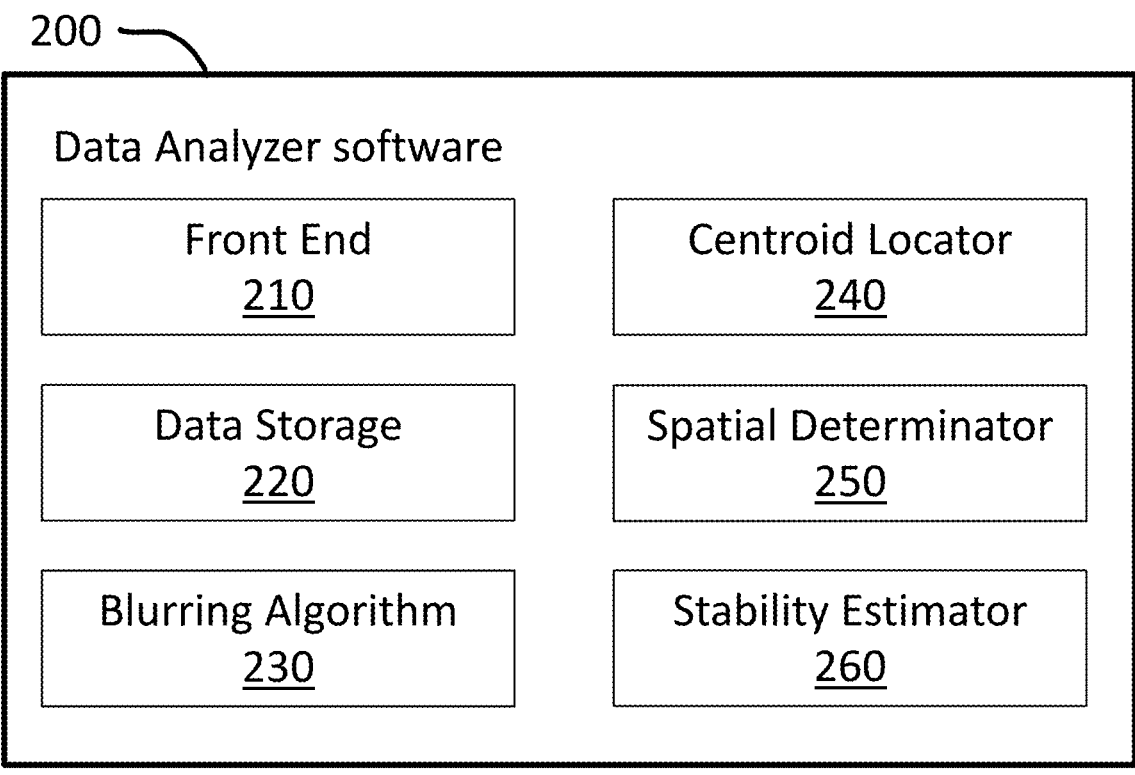
FIG. 2 is a block diagram illustrating the major software components of an exemplary data analyzer component of an implant stability sensor system in accordance with an example of the present application.

FIG. 2 is a simplified block diagram of various software components of an exemplary data analyzer component of an implant stability sensor system as disclosed herein. As shown, data analyzer software 200 can include front end 210, data storage 220, blurring algorithm 230, centroid locator 240, spatial determinator 250, and stability estimator 260.

Front end 210 can include instructions for receiving images from a camera and signals from a torque wrench or another force inducer equipped with a sensor to record and transmit force signals. In some embodiments, front end 210 can include instructions for receiving torque wrench data over a radio signal. In some embodiments, the radio signal is a Bluetooth signal.

In some embodiments, front end 210 can include instructions for receiving camera images over a hard-wired cable. In other embodiments, front end 210 can include instructions for receiving camera images over a radio signal. In some embodiments, the radio signal may include Bluetooth, Near-Field communication, other radiofrequency communication, LTE, 5G, Zigbee, and the like.

Data storage 220 can include instructions for depositing torque wrench data and/or camera image data into computer memory and make the data available for other modules.

Blurring algorithm 230 can include steps for receiving images from data storage 220 and softening the contrasting spot to a standardized blur pattern recognizable by centroid locator 240. In some embodiments, blurring algorithm 230 can include steps for rejecting noise due to low light, background, texture, shadows, or reflections. In some embodiments, the blurring algorithm can include portions of software applications such as Median Blur, Bilateral Filter, or Gaussian Blur.

Centroid locator 240 can include instructions for analyzing a blurred spot within an image to provide a centroid. In some embodiments, the centroid can be expressed as an X-Y pixel grid location within the field of view of the camera. In some embodiments, the centroid may be assigned a grid location within the field of view. In some embodiments, the X-Y pixel grid location for each image is reported to spatial determinator 250.

In some embodiments, centroid locator can include portions of edge detection software such as Canny Edge Detection or an Astronomical Image Processing algorithm.

Spatial determinator 250 can include instructions for analyzing the X-Y pixel grid location in successive images and outputting an indication corresponding to direction and amplitude of movement from one or more previous images. In some embodiments, spatial determinator 250 may associate torque wrench data with image data in the time domain. In some embodiments, spatial determinator 250 may report a timestamp along with the indication of direction and amplitude. In some embodiments, the spatial determinator 250 can include portions of software such as ImageJ or other suitable spatial determination software.

Stability estimator 260 may include instructions for analyzing timestamp, direction, and/or amplitude and providing a trending analysis. In some embodiments, stability estimator 260 may output a total excursion value of implant movement from a rest position when a force is applied by a torque wrench or when the force applied by a torque wrench is at a pre-set torque value. In some embodiments, a stability estimate may include direction and amplitude of implant movement from a rest position while a gradually increasing force is applied by a torque wrench and when the force applied by a torque wrench reaches a pre-set torque value. In some embodiments, stability estimator 260 may provide an estimate of implant fit to indicate poor implant fit needing more work, good implant fit suitable for cemented fixation, or superior implant fit suitable for a cementless fixation. In some embodiments, the estimate of implant fit indicates a good implant fit suitable for cemented fixation if a relative motion of the implant and bone from the images before and during application of force is determined to be more than about 50 microns; about 50 microns to about 100 microns; about 50 microns to about 75 microns; etc. In some embodiments, the estimate of implant fit indicates an improved implant fit suitable for a cementless fixation if a relative motion of the implant and bone from the images before and during application of force is determined to be less than or equal to about 50 microns; about 0 microns to about 50 microns; about 25 microns to about 50 microns; about 0 microns to about 25 microns; etc.

Figure 3:
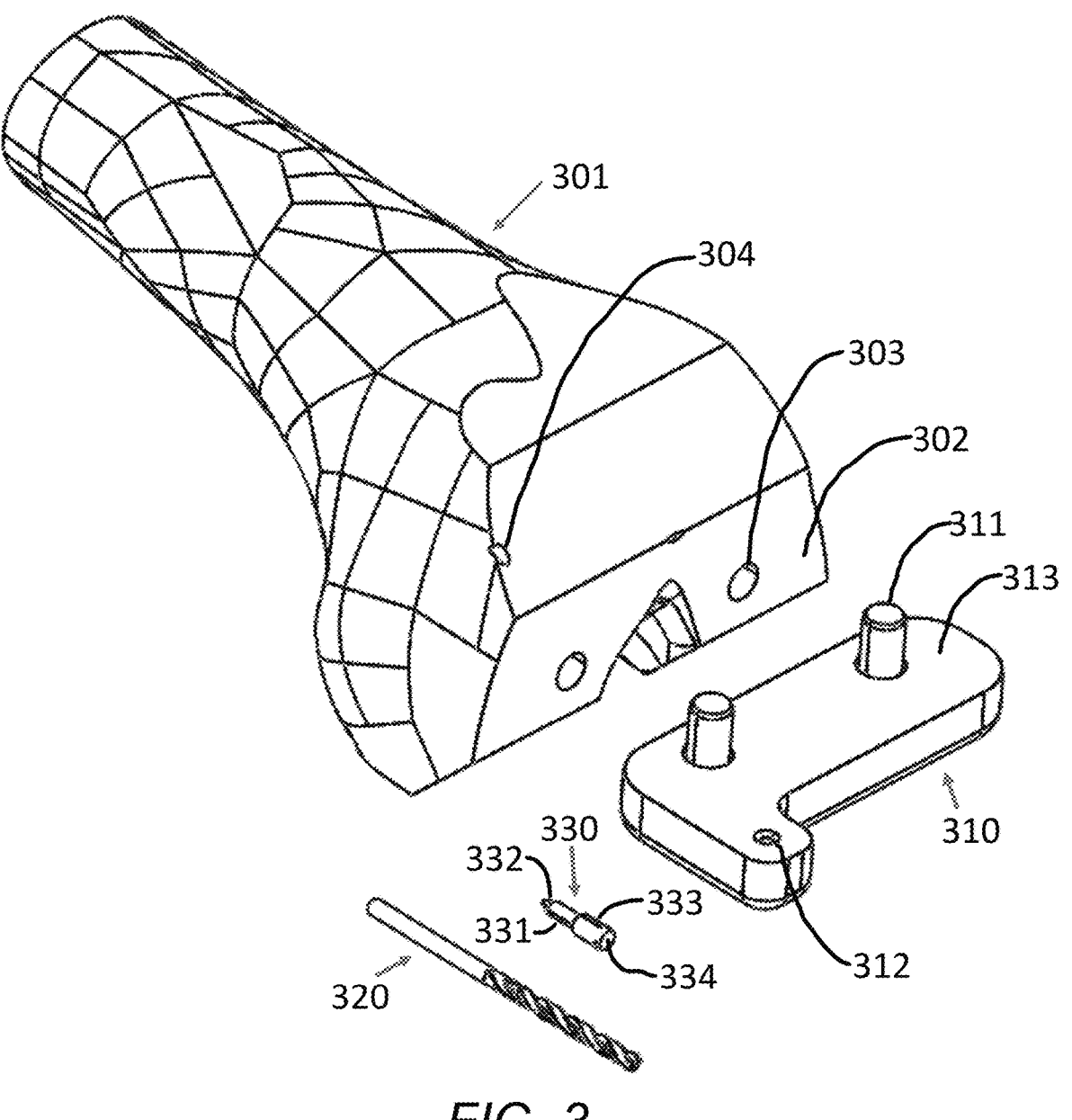
FIG. 3 is a perspective view of a bone, the system including a drill guide, a drill, and marking pin in accordance with an example of the present application.

FIG. 3 illustrates an exemplary guide plate 310 for removable attachment to a bone 301. Bone 301 can be any bone, including the ends of bones involved in joint replacement surgery. Common examples are the distal femur, involved in knee replacement surgery, the proximal femur, involved in hip joint surgery, and the proximal humerus, involved in shoulder surgery.

Bone 301 may include surgically prepared features such as substantially flat faces 302 and substantially cylindrical openings 303. Guide plate 310 may include one or more substantially flat surfaces 313 intended to abut one or more flat faces 302 of the bone. Guide plate 310 may include one or more engagement features 311 which may be substantially cylindrical dowel pins that can engage with one or more substantially cylindrical openings 303. Guide plate 310 may include one or more drill apertures 312 for guiding and providing precise alignment for drill 320.

In some embodiments, marking pin 330 may be made of plastic or other suitable material. In some embodiments, marking pin 330 may be for removable attachment to a bone 301.

A first portion 331 of marking pin 330 may include a cylindrical shape of substantially equal diameter as drill 320, providing a slip fit into a clearance hole 304. Marking pin 330 may be provided with a tapered tip 332 to facilitate entry into clearance hole 304.

A second portion 333 of marking pin 330 may be include a larger diameter than first portion 331 to act as an insertion limit stop. The length of second portion 333 can determine the distance of visual surface 334 from the bone. Visual surface 334 may be polished, plated, colored, or textured as appropriate to provide improved optical contrast with the surrounding bone, tissue, fluids, tools, and other items associated with a surgical field.

A bone locator may include a well-defined shape (e.g., circle, square, dot, etc.) that is substantially free of edge fuzziness. This can be accomplished by a preprinted dot or shape or with a suitable marking instrument. Multiple bone locators may also be in the same plane, as described elsewhere herein, to allow for a more accurate centroid and measurement determination. The centroid and height of multiple bone locators may reduce measurement "noise".

Figure 4:
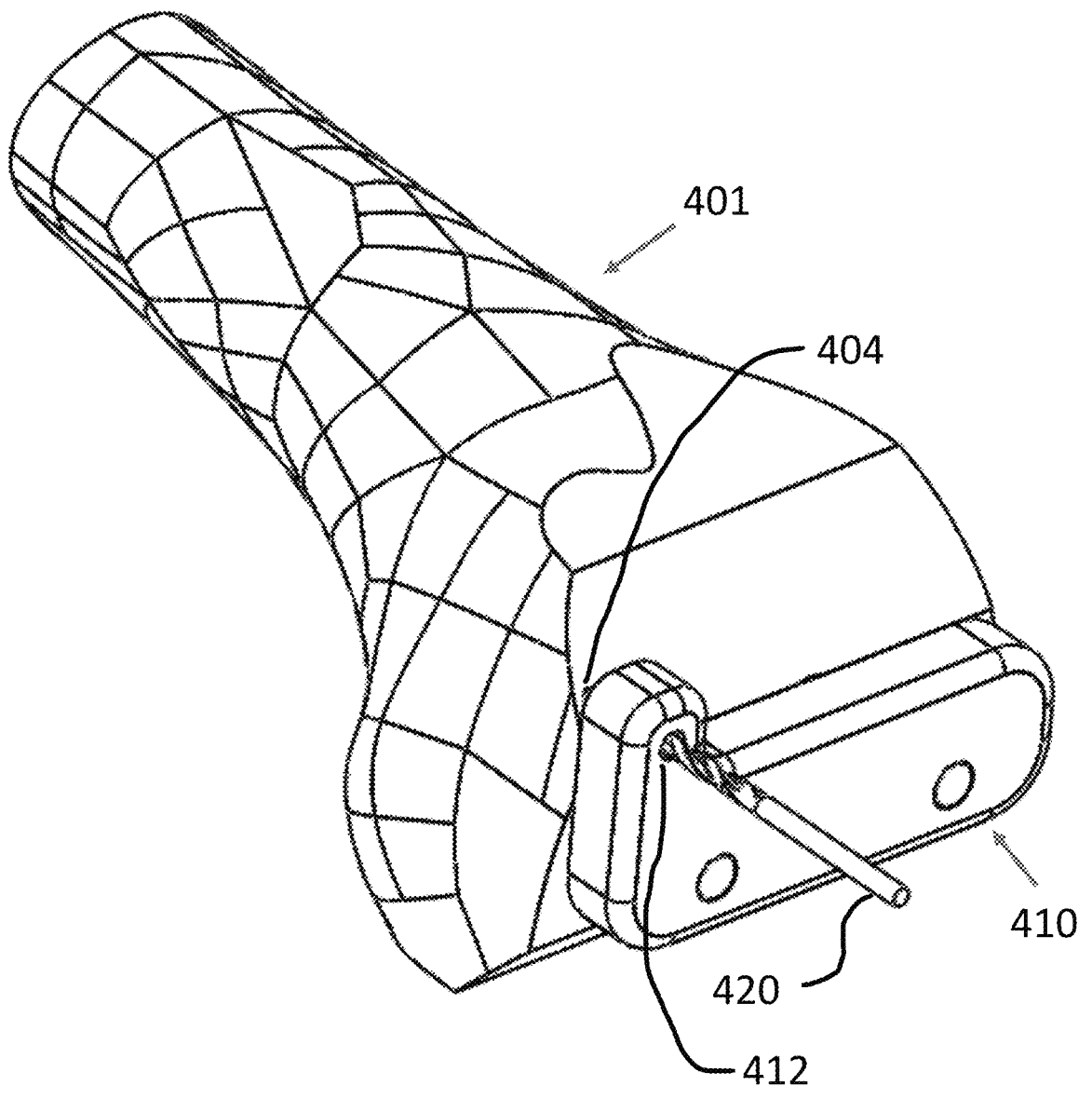
FIG. 4 is a perspective view of a bone, the system including a drill guide and a drill in accordance with an example of the present application.

FIG. 4 illustrates an exemplary guide plate 410 located and abutted to a bone 401. A drill 420 may be used to produce hole 404 when guided by drill aperture 412 of guide plate 410. Rotational energy is provided by a drill motor (not shown). Following the drilling operation, the drill motor, drill 420, and guide plate 410 are removed leaving hole 404 available for insertion of a marking pin.

Figure 5:
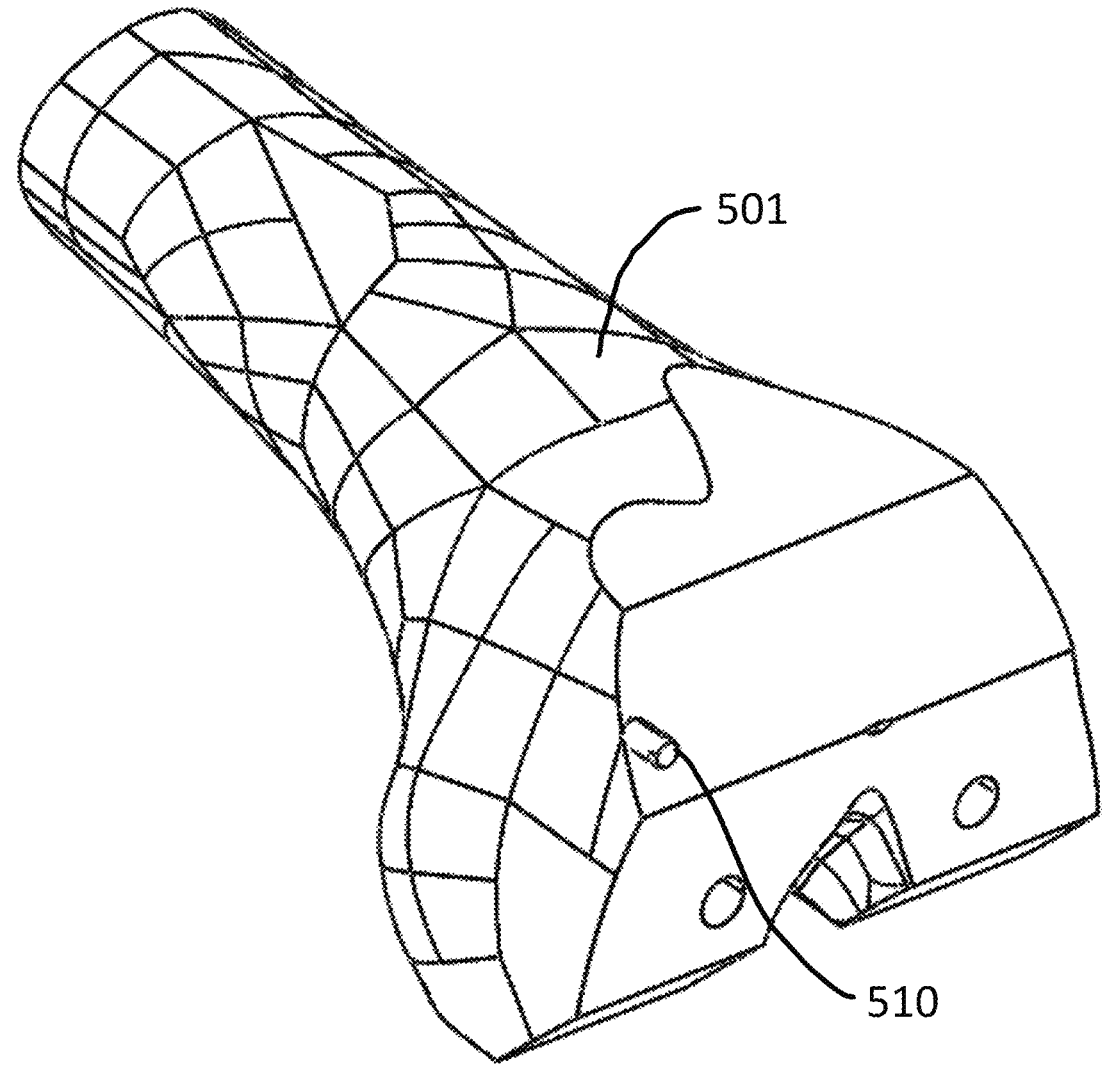
FIG. 5 is a perspective view of a bone, the system including a marking pin in accordance with an example of the present application.

FIG. 5 illustrates an exemplary marking pin 510 partially residing within a drilled hole produced by the previous drilling operation of FIG. 4. Marking pin 510 may be placed so that it remains visible for a portion of the surgery. In some embodiments, marking pin 510 may be removed following completion of the implant stability sensor procedure.

Figure 6:
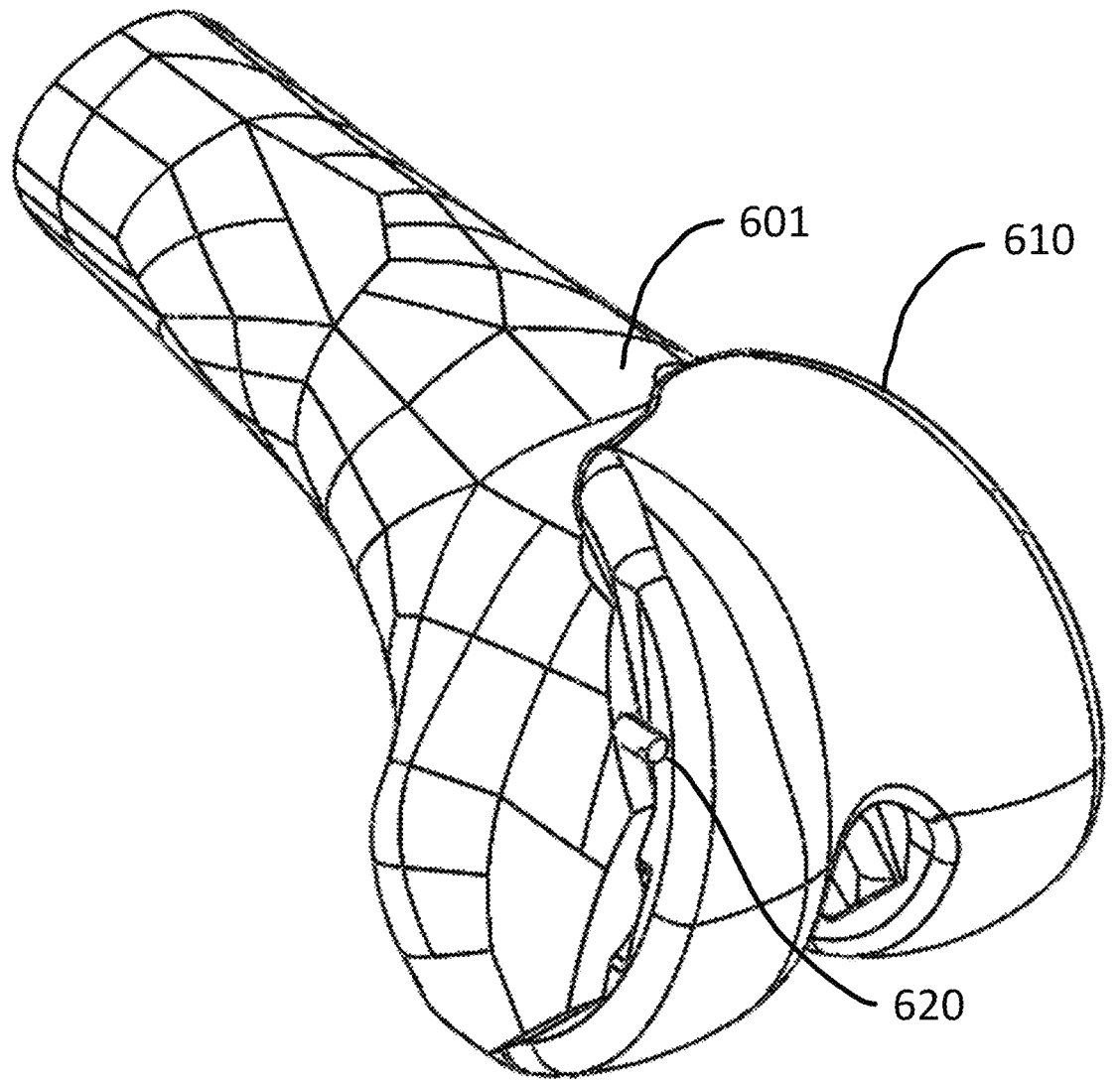
FIG. 6 is a perspective view of a bone with implant, the system including a marking pin in accordance with an example of the present application.

FIG. 6 illustrates an exemplary marking pin 620 shown attached to bone 601 and located outside the perimeter of implant 610.

Figure 7:
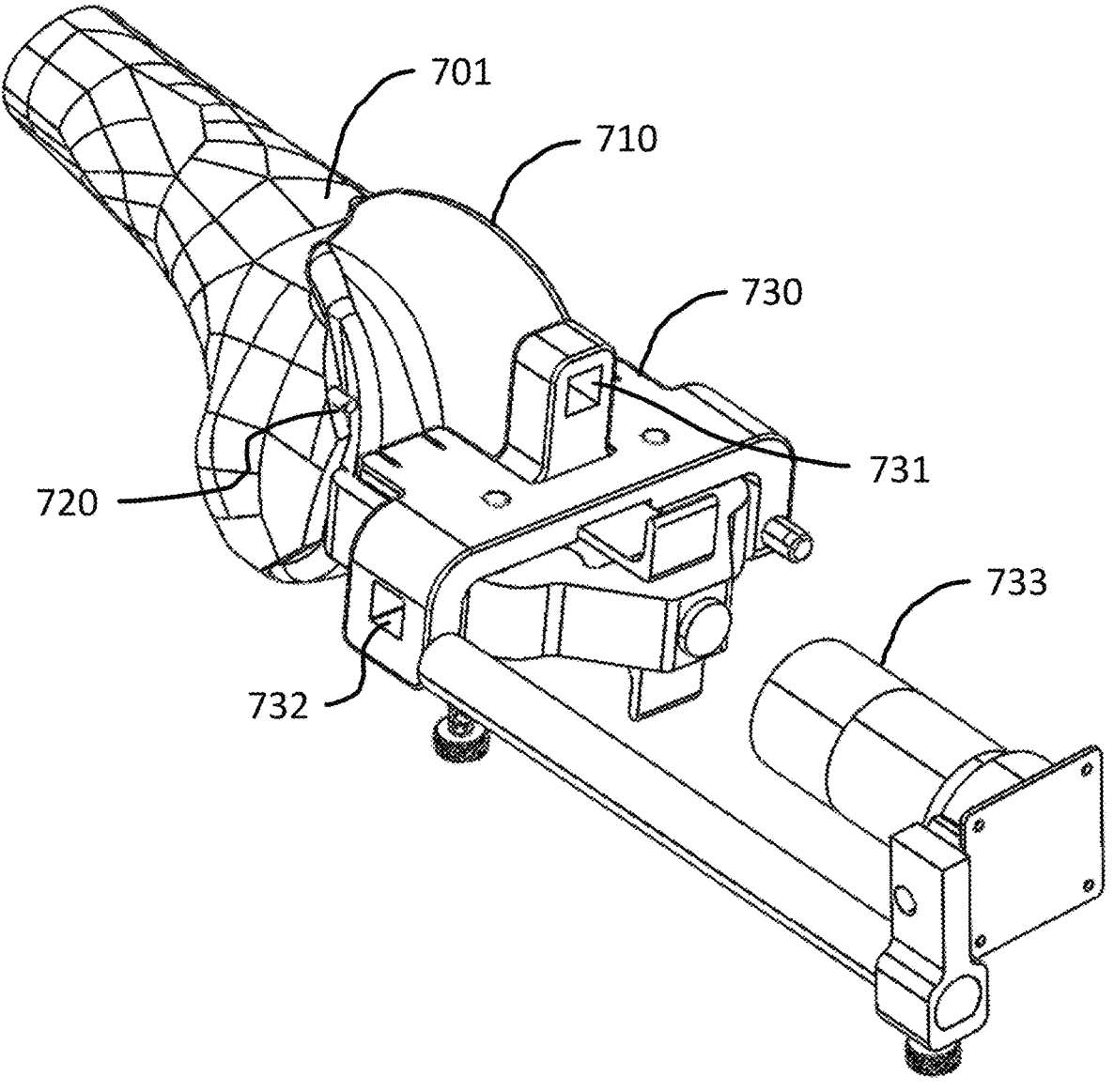
FIG. 7 is a perspective view of a bone with implant, the system including a marking pin, clamp, and camera in accordance with an example of the present application.

FIG. 7 illustrates an exemplary marking pin 720 coupled to bone 701, clamp 730 coupled to implant 710, and camera 733 coupled to clamp 730. Drive aperture 731 can be formed as part of clamp 730 and configured with an axis of rotation substantially in line with the axis of bone 701. When torque is applied to drive aperture 731, rotational forces are transferred to implant 710 substantially in line with the axis of bone 701. Drive aperture 732 is formed as part of clamp 730 and configured with an axis of rotation substantially transverse with the axis of bone 701. When torque is applied to drive aperture 731, rotational forces are transferred to implant 710 substantially transverse with the axis of bone 701. In some embodiments, other drive apertures may be configured with other axes of rotation to suit the needs of the implant and bone geometries. Various forces applied in various axes of rotation are assumed to cause detectable movement of implant 710 relative to bone 701.

The exemplary system further includes camera 733 rigidly fixed to clamp 730. The camera 733 may function to follow any movement of clamp 730. Camera 733 can include a field of view, substantially directed toward marking pin 720, and focused to provide a sharp image of marking pin 720. By virtue of the fixed engagements of camera 733 to clamp 730 and clamp 730 to implant 710, camera 733 is intended to move along with implant 710.

From the frame of reference of the camera, movement of marking pin 720 within the field of view of camera 733 may be considered as a proxy for movement of implant 710 relative to bone 701.

Figure 8:
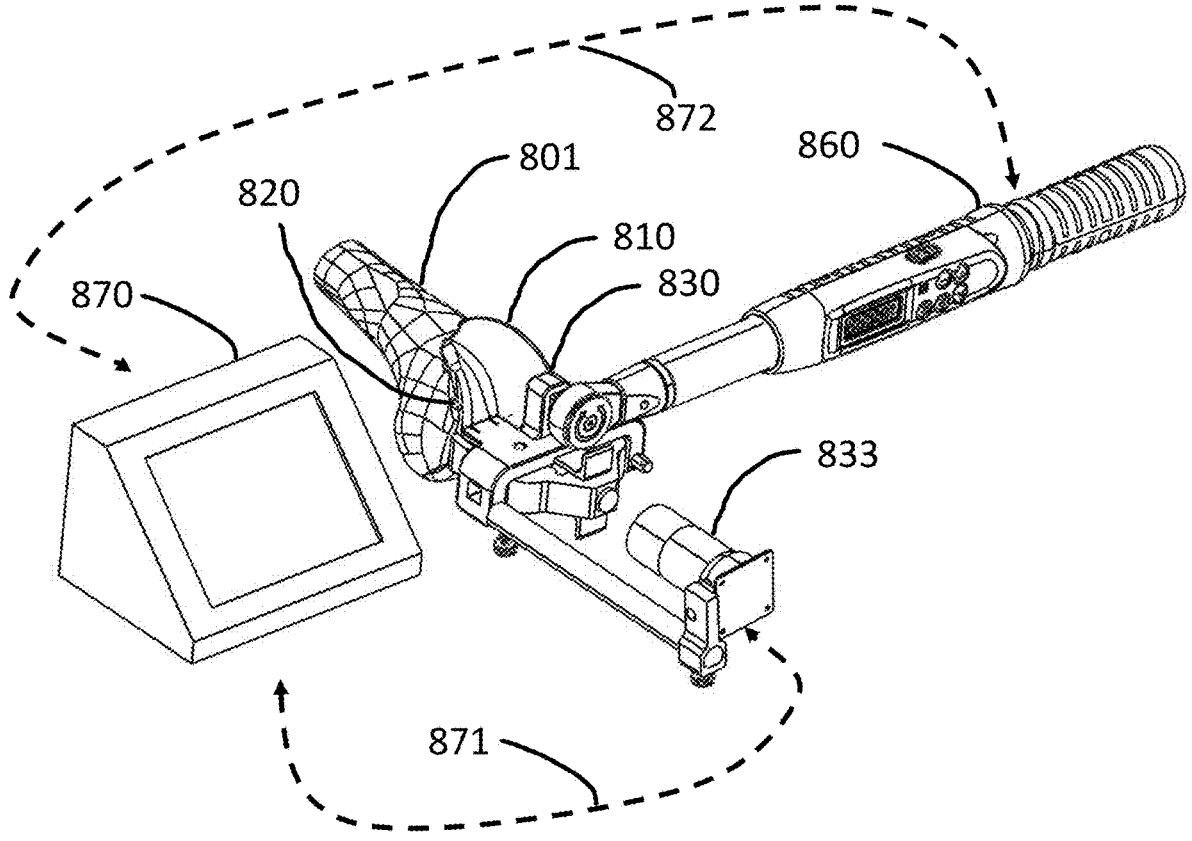
FIG. 8 is a perspective view of a bone with implant, the system including a marking pin, clamp, camera, torque wrench, and electronics in accordance with an example of the present application.

FIG. 8 illustrates an exemplary implant stability sensor system for use in a knee joint surgery. System can include a torque wrench 860 engaged with a drive aperture of clamp 830. Torque wrench 860 can apply forces to implant 810 via clamp 830. Torque wrench 860 may report the torque value continuously or at intervals as torque is gradually increased from zero to a pre-set torque value. At a pre-set torque value, torque wrench 860 may report an audible sound or radio signal. In some embodiments, torque wrench 860 communicates with data analyzer 870 over transmission pathway 872.

Also illustrated is camera 833 which captures images of marking pin 820. In some embodiments, camera 833 communicates with data analyzer 870 over transmission pathway 871. In some embodiments, data analyzer 870 time aligns data from camera 833 and torque wrench 860 and produces a result as described elsewhere herein.

Although data analyzer 870 is shown as a local computing device, one of skill in the art will appreciate that the functions of data analyzer 870 may be a smart phone or tablet, or a remote computing device, like a workstation, server, and the like. Further, although one computing device is shown, one of skill in the art will appreciate that one or more computing devices may be used. For example, in some embodiments, a first computing device may include instructions stored in memory for analyzing one or more images;

and a second computing device may include instructions stored in memory for displaying one or more outputs. The first and second computing devices may be communicatively coupled while one or both of the first or second computing devices may be communicatively coupled to camera assembly 833.

Figure 9:
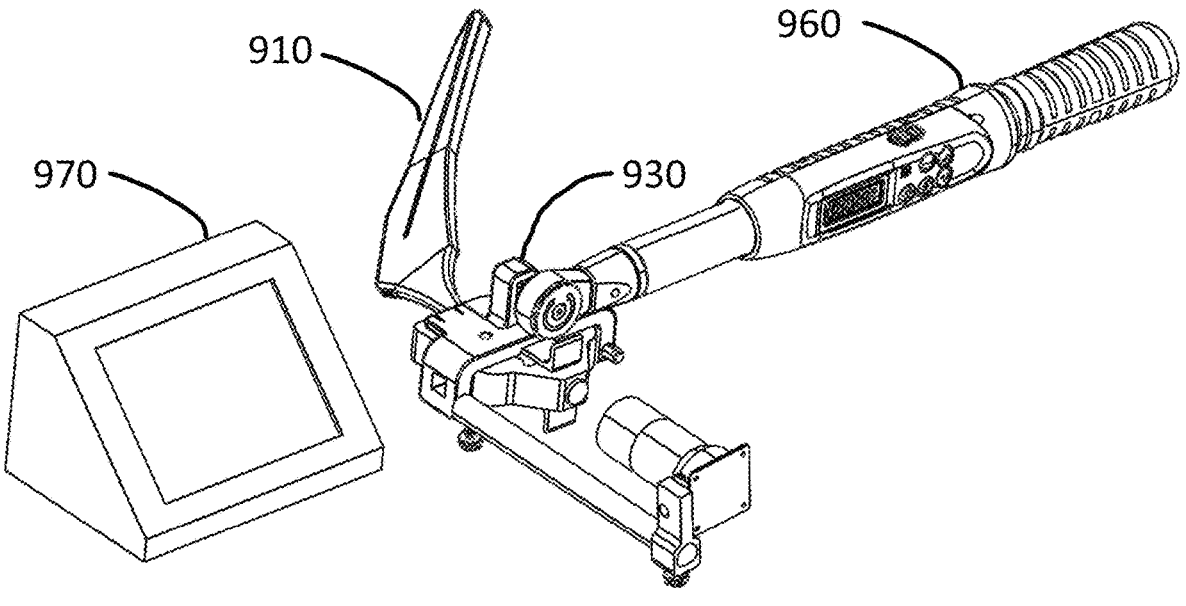
FIG. 9 is a perspective view of a hip implant, the system including a clamp, camera, torque wrench, and electronics in accordance with an example of the present application.

FIG. 9 illustrates an exemplary implant stability sensor system for use in a hip joint surgery. In some embodiments, clamp 930 can engage features of hip implant 910. Other aspects of the implant stability sensor system remain as described elsewhere herein.

Figure 10:
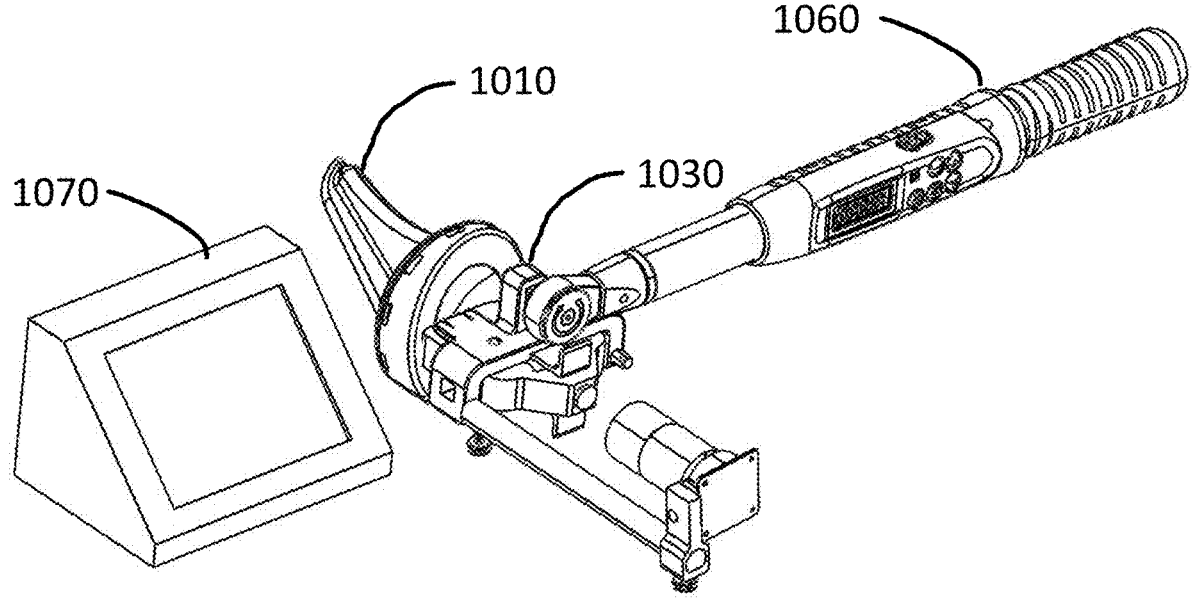
FIG. 10 is a perspective view of a shoulder implant, the system including a clamp, camera, torque wrench, and electronics in accordance with an example of the present application.

FIG. 10 illustrates an exemplary implant stability sensor system for use in a shoulder implant. In some embodiments, clamp 1030 can engage features of shoulder implant 1010. Other aspects of the implant stability sensor system remain as described elsewhere herein.

Methods

The methods described herein function to measure implant stability. In some embodiments, the methods function to detect relative motion between a bone implant and the bone. In some embodiments, the methods are used for implant surgery, but can additionally or alternatively be used for any suitable applications, clinical or otherwise. The method can be configured and/or adapted to function for any suitable motion measurement.

In various embodiments, some of the methods can be partially or wholly computer-implemented. In some of these embodiments, the motion detector of FIG. 1 separately or in combination with the data analyzer of FIGS. 1-2 can perform at least a portion of the methods described herein.

Figure 11:
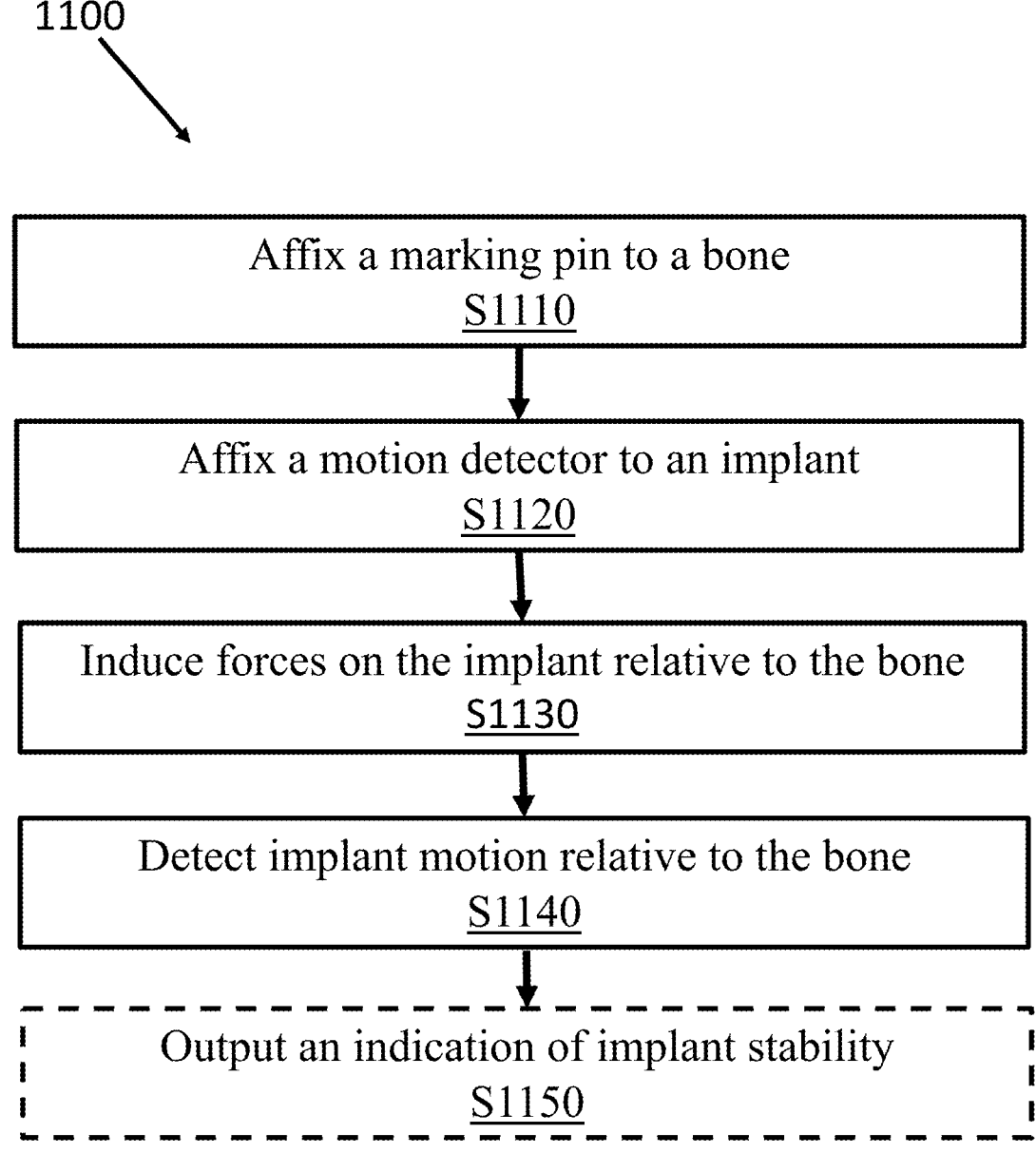
FIG. 11 is a flow diagram of an exemplary method for operating an implant stability sensor in accordance with an example of the present application.

FIG. 11 is a flow diagram of an exemplary method 1100 for operating an implant stability sensor system. As shown, implant stability sensor system method 1100 includes affixing a marking pin to a bone in block S1110, affixing a motion detector to an implant at block S1120, inducing forces on the implant relative to the bone at block S1130, detecting implant motion relative to the bone at block S1140, and, optionally, outputting an indication of implant stability at block S1150.

In some embodiments, the method 1100 includes affixing a marking pin to a bone in block S1110. The marking pin can be considered a bone locator, as described herein in some embodiments. The marking pin can be affixed to the bone by a variety of techniques including, but not limited to, those described herein in FIGS. 3-6 in some embodiments.

In some embodiments, the method 1100 includes affixing a motion detector to an implant at block S1120. The motion detector can include a machine vision device including a camera, as described herein in FIGS. 1-2 and 7-8 in some embodiments.

In some embodiments, the method 1100 includes inducing forces on the implant relative to the bone. The force can be induced on the implant by a force inducer as described herein in FIGS. 1-8, in some embodiments. In some embodiments, the force inducer is an electronic torque wrench configured to manually induce the force on the implant in a variety of directions on the bone including, but not limited to, a direction axial, transverse vertical, transverse horizontal, or rotational relative to the bone.

In some embodiments, the method 1100 includes detecting motion relative to the bone at block S1140. In some embodiments, images of the marking pin are captured by the motion detector before and/or during the application of force. In such embodiments, a detected change or difference in location of the marking pin in at least a first and second photo of the plurality of photos determines a relative motion of the bone. In these embodiments, the relative motion is then based on the difference between the second and first location. In some embodiments, the force inducer includes a sensor capable of detecting force signals that can be associated with at least a portion of the plurality of images captured during the application of force. For example, in some embodiments, a first location of the marking pin can be determined in a first photo when the implant is at rest and a second location of the marking pin can be determined in a second photo when the implant is under a force. In various embodiments, the data analyzer of FIGS. 1-2 determines the relative motion.

In some embodiments, the method 1100 optionally includes outputting an indication of implant stability. In some embodiments, the outputting of an indication of implant stability can be performed by the data analyzer of FIG. 1 or the stability estimator of FIG. 3. In some embodiments, the output of an indication of implant stability occurs when the relative motion is determined to be either more than about 50 microns; about 50 microns to about 100 microns; about 50 microns to about 75 microns; less than or equal to about 50 microns; about 0 microns to about 50 microns; about 25 microns to about 50 microns; about 0 microns to about 25 microns; etc.

Figure 12:
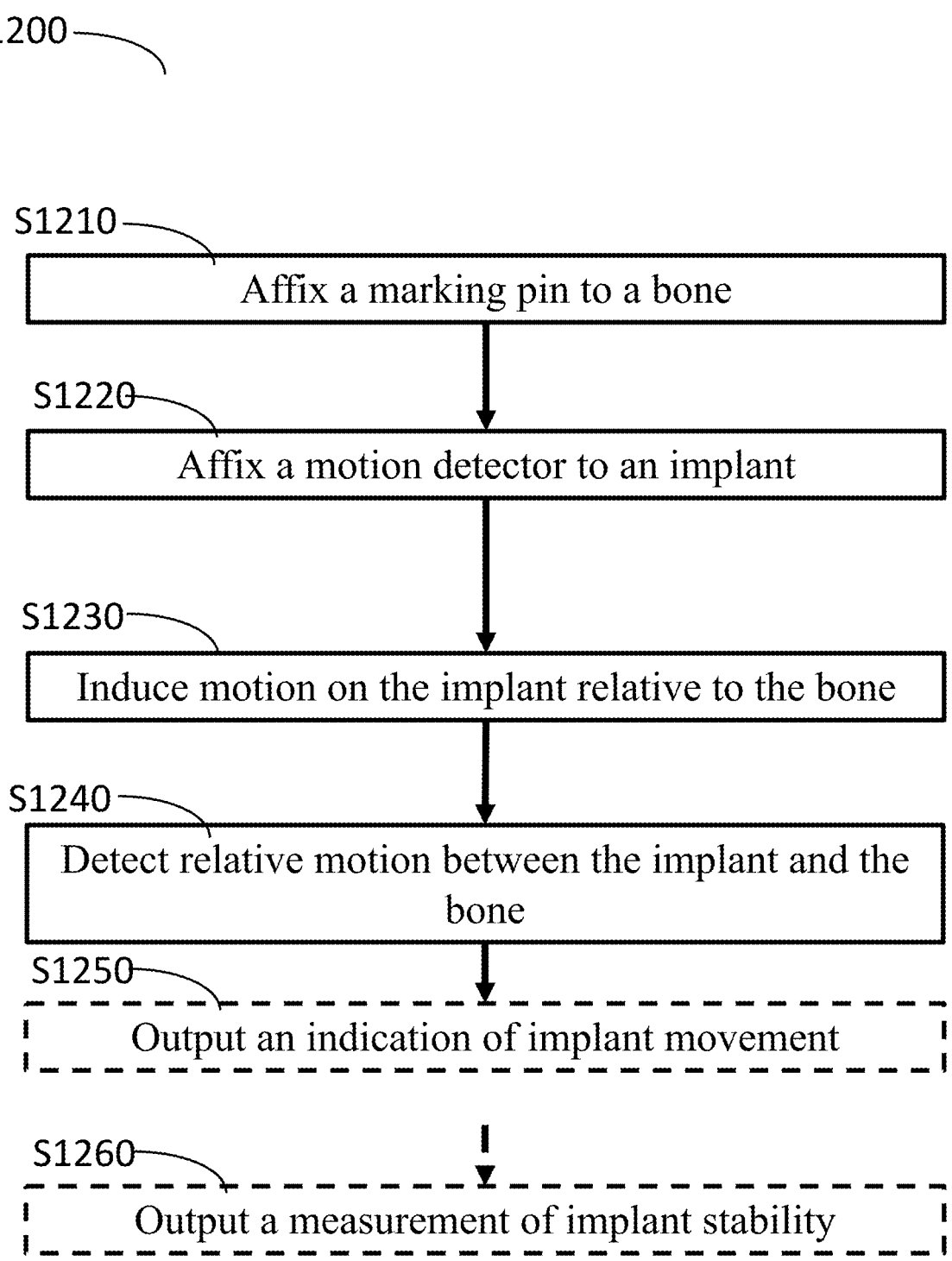
FIG. 12 is a flow chart of a method according to another example of the present application.

As shown in FIG. 12, a method 1200 for measuring implant stability of one embodiment includes affixing a marking pin to a bone at block S1210, affixing a motion detector to an implant at block S1220, inducing forces on the implant at block S1230, detecting relative motion between the implant and the bone at block S1240, optionally outputting an indication of implant movement at block S1250, and optionally outputting a measurement of implant stability at block S1260. In some embodiments, the method steps S1210-S1240 and S1260 can be performed similarly to as described herein in FIG. 11.

In some embodiments, the method 1200 optionally includes outputting an indication of implant movement at block S1250. In some embodiments, this output is based on the determined relative motion from block S1240.

Figure 13:
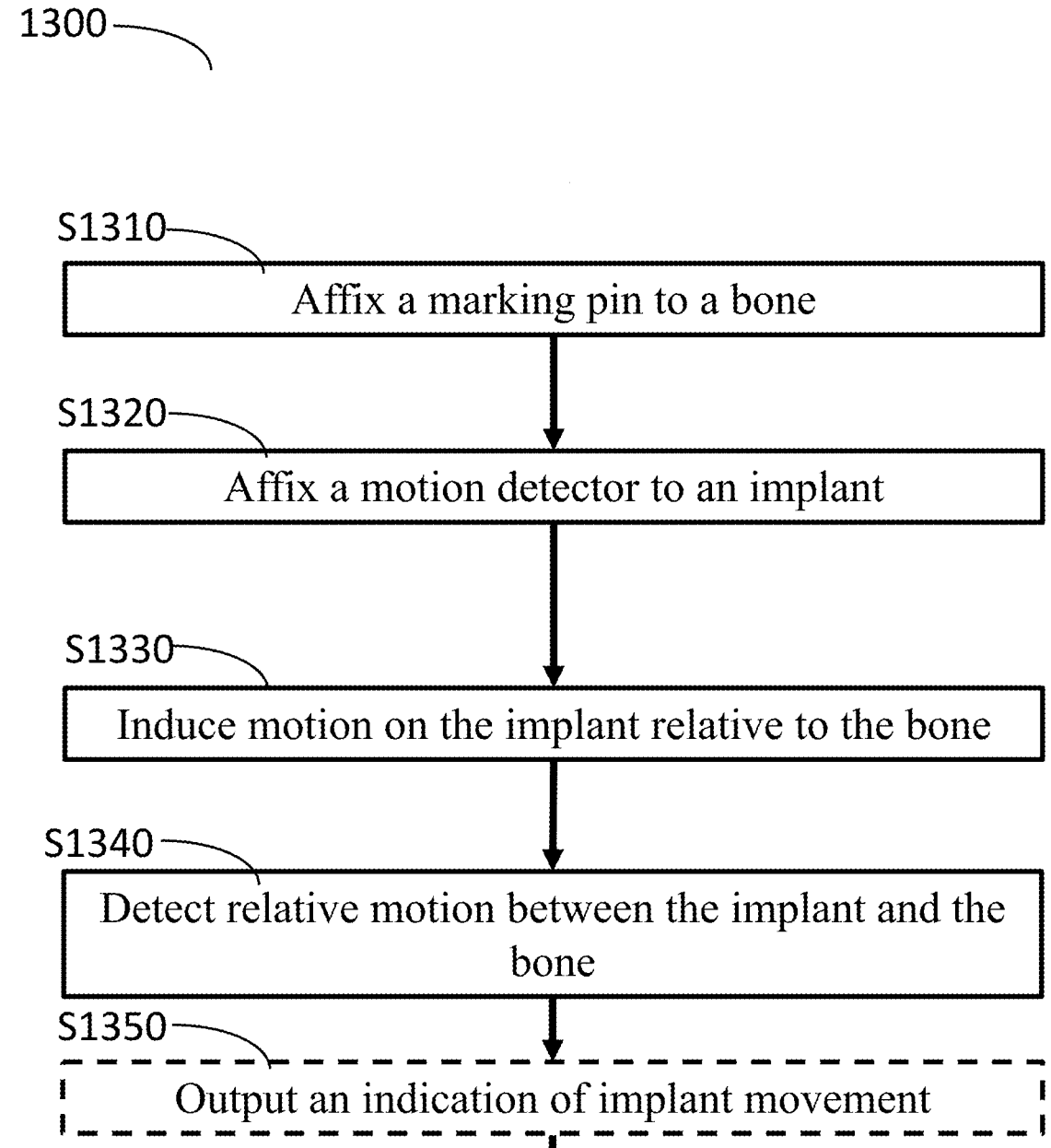
FIG. 13 is a flow chart of a method according to another example of the present application.

As shown in FIG. 13, a method 1300 for measuring implant stability includes: affixing a marking pin to a bone at block S1310, affixing a motion detector to an implant at block S1320, inducing forces on the implant at block S1330, detecting relative motion between the implant and the bone at block S1340, optionally outputting an indication of implant movement at block S1350, optionally outputting a measurement of implant stability at block S1360, and optionally outputting a recommendation of whether the implant should be cemented or cementless at block S1370. In some embodiments, the method steps S1310-S1360 can be performed similarly to as described herein in FIG. 11.

In some embodiments, the method 1300 optionally includes outputting a recommendation of whether the implant should be cemented or cementless at block S1370. In some embodiments, the outputting of a recommendation that the implant should be cemented occurs when the relative motion is determined to be more than about 50 microns, and the outputting of a recommendation that the implant should be cementless occurs when the relative motion is determined to be less than or equal to about 50 microns.

As shown in FIG. 14, a method 1400 for measuring implant stability includes affixing a motion detector to a bone at block S1410, affixing a strike pad to an implant at block S1420, using an impactor to induce forces on the implant at block S1430, detecting relative motion between the implant and the bone at block S1440, optionally outputting an indication of implant movement relative to the bone at block S1450, optionally outputting a measurement of implant stability at block S1460, and optionally outputting a recommendation whether the implant should be cemented or cementless at block S1470. In some embodiments, the method 1400 can be performed similarly to as described herein in FIG. 13 but with an alternative force inducer.

As shown in FIG. 15, a method 1500 for measuring implant stability including affixing a motion detector to a bone at block S1510, affixing a vibrator to an implant at block S1520, using the vibrator to induce forces on the implant at block S1530, detecting relative motion between the implant and the bone at block S1540, optionally outputting an indication of implant movement relative to the bone at block S1550, optionally outputting a measurement of implant stability at block S1560, and optionally outputting a recommendation of whether the implant should be cemented or cementless at block S1570. In some embodiments, the method 1500 can be performed similarly to as described herein in FIG. 13 but with an alternate force inducer.

As shown in FIG. 16, a method 1600 for measuring implant stability includes affixing a motion detector to a bone at block S1610, affixing an impulse generator to an implant at block S1620, using the impulse generator to induce forces on the implant at block S1630, detecting relative motion between the implant and the bone at block S1640, outputting an indication of implant movement relative to the bone at block S1650, optionally outputting a measurement of implant stability at block S1660, and optionally outputting a recommendation whether the implant should be cemented or cementless at block S1670. In some embodiments, the method 1600 can be performed similarly to as described herein in FIG. 13 but with an alternative force inducer.

As shown in FIG. 17, a method 1700 for measuring implant stability includes affixing a reflector to a bone at block S1710, affixing a laser and photodetector to an implant at block S1720, inducing forces on the implant at block S1730, detecting relative motion between the implant and the bone at block S1740, optionally outputting an indication of implant movement relative to the bone at block S1750, optionally outputting a measurement of implant stability at block S1760, and optionally outputting a recommendation whether the implant should be cemented or cementless at block S1770.

As shown in FIG. 18, a method 1800 for measuring implant stability includes affixing a first attachment point of a strain gauge to a bone at block S1810, affixing a second attachment point of said strain gauge to an implant at block S1820, inducing forces on the implant at block S1830, detecting relative motion between the implant and the bone at block S1840, outputting an indication of implant movement relative to the bone at block S1850, optionally outputting a measurement of implant stability at block S1860, and optionally outputting a recommendation whether the implant should be cemented or cementless at block S1870.

As shown in FIG. 19, a method 1900 for measuring implant stability including affixing first attachment points of multiple strain gauges to a bone at block S1910, affixing second attachment points of said multiple strain gauges to an implant at block S1920, inducing forces on the implant at block S1930, detecting relative motion between the implant and the bone at block S1940, optionally outputting an indication of implant movement relative to the bone at block S1950, optionally outputting a measurement of implant stability at block S1960, and optionally outputting a recommendation whether the implant should be cemented or cementless at block S1970.

Figure 20:
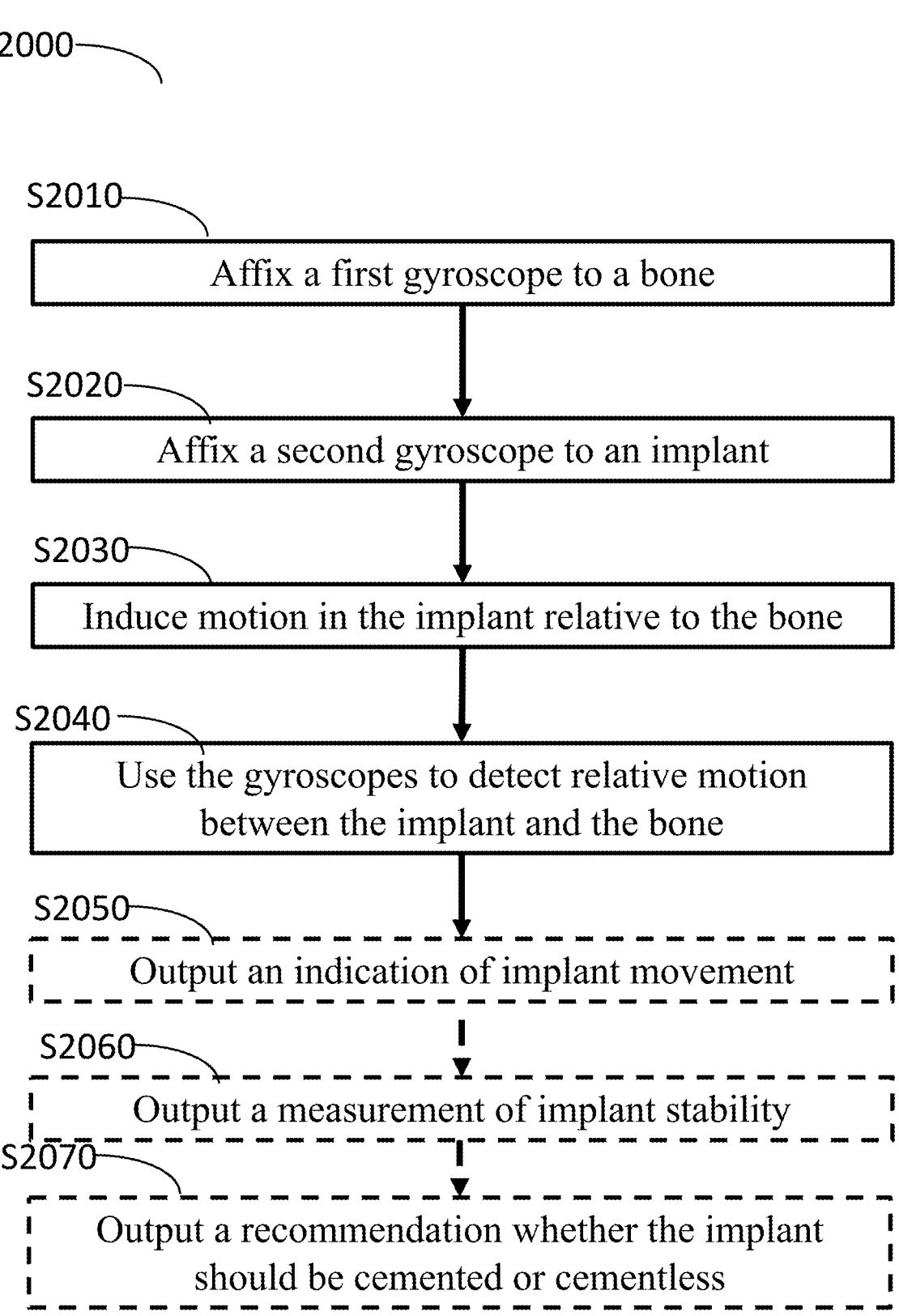
FIG. 20 is a flow chart of a method according to another example of the present application.

As shown in FIG. 20, a method 2000 for measuring implant stability including affixing a first gyroscope to a bone at block S2010, affixing a second gyroscope to an implant at block S2020, inducing forces on the implant relative to the bone at block S2030, detecting relative motion between the implant and the bone at block S2040, optionally outputting an indication of implant movement relative to the bone at block S2050, optionally outputting a measurement of implant stability at block S2060, and optionally outputting a recommendation whether the implant should be cemented or cementless at block S2070.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor on the analysis and display device. The analysis and display device may be a general-purpose computer, laptop, iPad, smart phone, or the like configured with suitable software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

EXAMPLES

Example 1. A system for detecting micromotion between a knee implant prosthesis and a bone comprising: a bone locator means, an implant attachment means, a detection means configured to detect relative micromotion between the bone and implant, a force inducing means, and a data analysis and display means.

Example 2. The system of any one of the preceding examples, but particularly Example 1, wherein the bone locator means includes a marking pin configured to reside in a drilled or threaded hole in the bone.

Example 3. The system of any one of the preceding examples, but particularly Example 1, wherein the bone locator means includes a visible mark using a marking medium from a list of ink, dye, or paint.

Example 4. The system of any one of the preceding examples, but particularly Example 1, wherein the implant attachment means includes a clamp.

Example 5. The system of any one of the preceding examples, but particularly Example 1, wherein the detection means includes a machine vision camera configured to generate images showing the location of the bone locator means within the camera's field of view.

Example 6. The system of any one of the preceding examples, but particularly Example 1, wherein the force inducing means includes a lever, breaker bar, or torque wrench configured to manually induce forces on the implant in a variety of directions relative to the bone including axial, transverse vertical, transverse horizontal, or rotational.

Example 7. The system of any one of the preceding examples, but particularly Example 1, wherein the data analysis and display means is configured to receive images from said camera, detect motion, and present an indication of implant movement relative to the bone.

Example 8. The system of any one of the preceding examples, but particularly Example 1, wherein the force inducing means includes an impactor configured to induce forces on the implant in a variety of directions relative to the bone including axial, transverse vertical, transverse horizontal, or rotational.

Example 9. The system of any one of the preceding examples, but particularly Example 1, wherein the force inducing means includes a vibrator configured to induce oscillatory forces on the implant in a variety of directions relative to the bone including axial, transverse vertical, transverse horizontal, or rotational.

Example 10. The system of any one of the preceding examples, but particularly Example 1, wherein the force inducing means includes an impulse generator configured to induce forces on the implant in a variety of directions relative to the bone including axial, transverse vertical, transverse horizontal, or rotational.

Example 11. The system of any one of the preceding examples, but particularly Example 1, wherein the bone locator means includes a reflector and the detection means includes a laser and a photodetector, fixed to the attachment means, said laser configured to illuminate said reflector, and said photo detector configured to receive light returning from said reflector.

Example 12. The system of any one of the preceding examples, but particularly Example 1, wherein the bone locator means includes a first attachment point of a strain gauge and wherein the detection means includes a second attachment point of said strain gauge.

Example 13. The system of any one of the preceding examples, but particularly Example 1, wherein the bone locator means includes multiple first attachment points of strain gauges and wherein the detection means includes multiple second attachment points of said strain gauges.

Example 14. The system of any one of the preceding examples, but particularly Example 1, wherein the bone locator means includes a first gyroscope fixed to a bone and configured to provide a data stream of its position, and wherein the detection means includes a second gyroscope, fixed to the implant attachment means and configured to generate a data stream of its position.

Example 15. A method of measuring implant stability comprising: affixing a marking pin to a bone; affixing a motion detector to an implant; inducing forces on the implant relative to the bone; detecting relative motion between the implant and the bone; and outputting an indication of implant movement.

Example 16. A method of any one of the preceding examples, but particularly Example 8 including the further step of providing a measurement of implant stability.

Example 17. A method of any one of the preceding examples, but particularly Example 9 including the further step of recommending whether the implant should be cemented or cementless.

Example 18. A method of measuring implant stability comprising the steps of affixing a strike pad to an implant, using an impactor to induce forces on the implant relative to the bone, detecting relative motion between the implant and the bone, and displaying an indication of implant movement relative to the bone.

Example 19. A method of measuring implant stability comprising: affixing a vibrator to an implant; using the vibrator to induce forces in the implant relative to the bone; detecting relative motion between the implant and the bone; and outputting an indication of implant movement relative to the bone.

Example 20. A method of measuring implant stability comprising the steps of affixing an impulse generator to an implant, using the impulse generator to induce forces on the implant, detecting relative motion between the implant and the bone, and displaying an indication of implant movement relative to the bone.

Example 21. A method of measuring implant stability comprising the steps of affixing a reflector to a bone, affixing a laser and photodetector to an implant, inducing force on the implant, detecting relative motion between the implant and the bone, and displaying an indication of implant movement relative to the bone.

Example 22. A method of measuring implant stability comprising the steps of affixing a first attachment point of a strain gauge to a bone, affixing a second attachment point of said strain gauge to an implant, inducing forces on the implant, detecting relative motion between the implant and the bone, and displaying an indication of implant movement relative to the bone.

Example 23. A method of measuring implant stability comprising the steps of affixing first attachment points of multiple strain gauges to a bone, affixing second attachment points of said multiple strain gauges to an implant, inducing forces on the implant, detecting relative motion between the implant and the bone, and displaying an indication of implant movement relative to the bone.

Example 24. A method of measuring implant stability comprising the steps of affixing a first gyroscope to a bone, affixing a second gyroscope to an implant, inducing forces on the implant, detecting relative motion between the implant and the bone, and displaying an indication of implant movement relative to the bone.

Example 25. The bone locator includes a visible mark using a marking medium from a list of ink, dye, or paint.

Example 26. The force inducing means includes a breaker bar, or torque wrench.

Example 27. The force inducing means includes an impactor.

Example 28. The force inducing means includes a vibrator.

Example 29. The force inducing means includes an impulse generator.

Example 30. The bone locator means includes a reflector and the detection means includes a laser and a photodetector.

Example 31. The bone locator means includes a first attachment point of a strain gauge and wherein the detection means includes a second attachment point of said strain gauge.

Example 32. The bone locator means includes multiple first attachment points of strain gauges and wherein the detection means includes multiple second attachment points of strain gauges.

Example 33. The bone locator means includes a first gyroscope fixed to a bone and configured to provide a data stream of its position, and wherein the detection means includes a second gyroscope, fixed to the implant attachment means and configured to generate a data stream of its position.

Example 34. The bone locator means includes a second marking pin or a plurality of marking pins or dots applied to the bone.

Example 35. The second marking pin or a plurality of marking pins or dots configured to improve camera resolution.

Example 36. The second marking pin or a plurality of marking pins or dots is configured to improve measurement accuracy.

Example 37. The second marking pin or the plurality of marking pins or dots form a plane substantially perpendicular to the camera optical axis so marking pins or dots remain in focus.

Example 38. The camera field of view is configured to take in a plurality of dots and form a constellation pattern recognizable by an Astronomical Image Processing algorithm.

Example 39. The camera and lens are employed to establish adequate field of view for measurement of the multiple dots or marks.

Example 40. The camera can have an external lens.

Example 41. The camera lens allows for adjustments field of view.

Example 42. The camera lens allows for adjustments of focal length.

Example 43. The camera lens helps prevent optical aberrations.

Example 44. The camera lens can be aspheric.

Example 45. The detection means can use computer software to establish a centroid for each mark or dot.

Example 46. The computer software can be ImageJ or other suitable spatial determination software.

Example 47. The detection means can use an edge detection algorithm to establish a centroid for each mark or dot.

Example 48. The edge detection algorithm can use off the shelf software applications (apps) such as Canny Edge Detection or an Astronomical Image Processing algorithm.

Example 49. The computer program can include a blurring algorithm to reject noise due to low light, background, texture, shadows, or reflections.

Example 50. The blurring algorithm can use Off-The-Shelf (OTS) software applications (apps) such as Median Blur, Bilateral Filter, or Gaussian Blur.

Example 51. The motion inducing means can include an electronic torque wrench.

Example 52. The electronic torque wrench can be configured to send signals to the data analysis and display means.

Example 53. The electronic torque wrench and data analysis and display means can be configured to communicate using Bluetooth technology.

Example 54. The electronic torque wrench can be configured to signal when a pre-determined torque is reached.

Example 55. The data analysis and display means can be configured to convert the torque measurement into a force acting upon the implant.

Example 56. The force inducing means can be configured to convert the torque measurement into a force acting upon the implant.

Example 57. The impactor firing can be configured in any suitable direction, timing, or repetition sequence.

Example 58. The force inducing means can be configured to include multiple impactors configured to attach both to the implant and to the bone.

Example 59. Multiple impactors can be configured to operate in a firing order sequence.

Example 60. Multiple impactors firing order sequence can be random or pseudo random.

Example 61. Multiple impactor firing order can be configured to induce oppositional forces on the bone and implant relative to each other.

Example 62. Multiple impactor firing order can be configured so one is firing in one direction while the other is firing in the opposite direction, for example one up the other down.

Example 63. The vibrator can be configured in any suitable direction, rotational direction, RPM, timing, or repetition sequence.

Example 64. The force inducing means can be configured to include multiple vibrator configured to attach both to the implant and to the bone.

Example 65. The multiple vibrators can be configured to operate in a timed sequence.

Example 66. The multiple vibrators timed sequence can be configured to induce oppositional forces on the bone and implant relative to each other.

Example 67. The multiple vibrators timing sequence can be configured so one is inducing forces in one direction while the other is inducing forces in the opposite direction, for example one up the other down at any moment in time.

Example 68. The systems, devices, and methods described herein can be employed for Total Hip Arthroplasty (THA) or Total Shoulder Arthroplasty (TSA).

Example 69. The systems, devices, and methods described herein can be configured to function for any suitable displacement measurement applications, clinical or otherwise.

Example 70. A system for detecting motion between an implant and a bone, the system comprising: a bone locator means configured to be coupled to the bone; and an implant attachment means configured to be coupled to the implant, wherein: the implant attachment means comprises a detection means, and the implant attachment means defines one or more apertures or surfaces for receiving a force from a force inducing means; and a data analysis means.

Example 71. The system of any one of the preceding examples, but particularly Example 70, wherein the bone locator means comprises a marking pin configured to reside in a drilled hole in the bone.

Example 72. The system of any one of the preceding examples, but particularly Example 70, wherein the implant attachment means comprises a clamp.

Example 73. The system of any one of the preceding examples, but particularly Example 70, wherein the detection means comprises a machine vision camera configured to generate a plurality of images showing a location of the bone locator means.

Example 74. The system of any one of the preceding examples, but particularly Example 73, wherein the system further comprises a sensor, and the data analysis means comprises a processor and a memory, wherein the processor is configured to: receive the plurality of images from the camera, receive, from the sensor, force signals indicative of forces induced on the implant being coupled to the bone; determine the location of the bone locator means in each of the plurality of images, determine a relative motion of the implant based on a change in the location of the bone locator means in each of the plurality of images, and output an indication of the relative motion of the implant relative to the bone based on the change in the location.

Example 75. The system of any one of the preceding examples, but particularly Example 74, wherein the receiving the plurality of images from the camera occurs before and during the receiving the force signals.

Example 76. The system of any one of the preceding examples, but particularly Example 70, further comprising the force inducing means.

Example 77. The system of any one of the preceding examples, but particularly Example 76, wherein the force inducing means is a lever, a breaker bar, a torque wrench, an electronic torque wrench, an impactor, a vibrator, or an impulse generator.

Example 78. The system of any one of the preceding examples, but particularly Example 77, wherein the force inducing means comprises the torque wrench configured to manually induce the force on the implant in a variety of directions relative to the bone.

Example 79. The system of any one of the preceding examples, but particularly Example 78, wherein the torque wrench is configured to manually induce the force on the implant in a direction axial, transverse vertical, transverse horizontal, or rotational relative to the bone.

Example 80. The system of any one of the preceding examples, but particularly Example 70, wherein the bone locator means comprises a defined shape configured for detection by the detection means.

Example 81. A computer-implemented method of measuring implant stability, the method comprising: receiving, from a detection means, a first image of a bone locator means affixed to a bone; determining a first location of the bone locator means in the first image; receiving, from a sensor, force signals indicative of forces induced on an implant being coupled to the bone; receiving, from the detection means, a second image of the bone locator means affixed to the bone; determining a second location of the bone locator means in the second image; determining a relative motion between the implant and the bone based on a difference between the second location and the first location; and outputting an indication of implant movement based on the determined relative motion.

Example 82. The method of any one of the preceding examples, but particularly Example 81, further comprising outputting a measurement of the implant stability.

Example 83. The method of any one of the preceding examples, but particularly Example 81, wherein the relative motion is determined to be either be more than about 50 microns or less than or equal to about 50 microns.

Example 84. The method of any one of the preceding examples, but particularly Example 82, further comprising outputting a recommendation of whether the implant should be cemented or cementless.

Example 85. The method of any one of the preceding examples, but particularly Example 84, wherein the outputting of the recommendation that the implant should be cemented occurs when the relative motion is determined to be more than about 50 microns; and wherein the outputting of the recommendation of that the implant should be cementless occurs when the relative motion is determined to be less than or equal to about 50 microns.

Example 86. The method of any one of the preceding examples, but particularly Example 81, wherein the determining the first location of the bone locator means in the first image occurs when the implant is at rest.

Example 87. The method of any one of the preceding examples, but particularly Example 81, wherein the determining the second location of the bone locator means in the second image occurs when the implant is under a force.

Example 88. A non-transitory computer-readable medium comprising computer-readable instructions, wherein the computer-readable instructions, when executed by a processor, cause the processor to perform operations comprising: receiving, from a detection means, a first image of a bone locator means affixed to a bone; determining a first location of the bone locator means in the first image; receiving, from a sensor, force signals indicative of forces induced on an implant being coupled to the bone; receiving, from the detection means, a second image of the bone locator means affixed to the bone; determining a second location of the bone locator means in the second image; determining a relative motion between the implant and the bone based on a difference between the second location and the first location; and outputting an indication of implant movement based on the determined relative motion.

Example 89. The non-transitory computer-readable medium of any one of the preceding examples, but particularly Example 88, wherein the determining the first location of the bone locator means in the first image occurs when the implant is at rest.

Example 90. The non-transitory computer-readable medium of any one of the preceding examples, but particularly Example 88, wherein the determining the second location of the bone locator means in the second image occurs when the implant is under a force.

Example 91. A system for detecting motion between an implant and a bone, the system comprising: a bone locator means configured to be coupled to the bone; an implant attachment means configured to be coupled to the implant, wherein: the implant attachment means comprises a detection means, and the implant attachment means defines one or more apertures or surfaces for receiving a force from a force inducing means; and a processor coupled to a memory and the detection means, wherein the memory comprises computer-readable instructions stored thereon that, when executed by the processor, cause the processor to perform operations comprising: receiving, from the detection means, a first image of the bone locator means coupled to the bone; determining a first location of the bone locator means in the first image; receiving, from a sensor communicatively coupled to the processor, force signals indicative of forces induced on the implant being coupled to the bone; receiving, from the detection means, a second image of the bone locator means coupled to the bone; determining a second location of the bone locator means in the second image; determining a relative motion between the implant and the bone based on a difference between the second location and the first location; and outputting an indication of implant movement based on the determined relative motion.

Example 92. The system of any one of the preceding examples, but particularly Example 91, wherein the determining the first location of the bone locator means in the first image occurs when the implant is at rest.

Example 93. The system of any one of the preceding examples, but particularly Example 91, wherein the determining the second location of the bone locator means in the second image occurs when the implant is under the force.

Example 94. A system for detecting motion between an implant and a bone, the system comprising: a bone locator configured to be coupled to the bone; an implant attachment configured to be coupled to the implant, wherein: the implant attachment comprises a detector, and the implant attachment defines one or more apertures or surfaces for receiving a force from a force inducer; and a processor coupled to a memory and the detector, wherein the memory comprises computer-readable instructions stored thereon that, when executed by the processor, cause the processor to perform operations comprising: receiving, from the detector, a first image of the bone locator coupled to the bone; determining a first location of the bone locator in the first image; receiving, from a sensor communicatively coupled to the processor, force signals indicative of forces induced on the implant being coupled to the bone; receiving, from the detector, a second image of the bone locator coupled to the bone; determining a second location of the bone locator in the second image; determining a relative motion between the implant and the bone based on a difference between the second location and the first location; and outputting an indication of implant movement based on the determined relative motion.

Example 95. The system of any one of the preceding examples, but particularly Example 94, wherein the bone locator comprises a marking pin configured to reside in a drilled hole in the bone.

Example 96. The system of any one of the preceding examples, but particularly Example 94, wherein the implant attachment comprises a clamp.

Example 97. The system of any one of the preceding examples, but particularly Example 94, further comprising the force inducer.

Example 98. The system of any one of the preceding examples, but particularly Example 97, wherein the force inducer is a lever, a breaker bar, a torque wrench, an electronic torque wrench, an impactor, a vibrator, or an impulse generator.

Example 99. The system of any one of the preceding examples, but particularly Example 98, wherein the force inducer comprises the torque wrench configured to manually induce the force on the implant in a variety of directions relative to the bone.

Example 100. The system of any one of the preceding examples, but particularly Example 99, wherein the torque wrench is configured to manually induce the force on the implant in a direction axial, transverse vertical, transverse horizontal, or rotational relative to the bone.

Example 101. The system of any one of the preceding examples, but particularly Example 94, wherein the determining the first location of the bone locator means in the first image occurs when the implant is at rest.

Example 102. The system of any one of the preceding examples, but particularly Example 94, wherein the determining the second location of the bone locator means in the second image occurs when the implant is under the force.

Example 103. The system of any one of the preceding examples, but particularly Example 94, wherein the instructions, when executed by the processor, further cause the processor to perform the operations comprising outputting a measurement of implant stability.

Example 104. The system of any one of the preceding examples, but particularly Example 94, wherein the relative motion is determined to be either be more than about 50 microns or less than or equal to about 50 microns.

Example 105. The system of any one of the preceding examples, but particularly Example 34, wherein the instructions, when executed by the processor, further cause the processor to perform the operations comprising outputting a recommendation of whether the implant should be cemented or cementless.

Example 106. The system of any one of the preceding examples, but particularly Example 36, wherein the outputting of the recommendation that the implant should be cemented occurs when the relative motion is determined to be more than about 50 microns; and wherein the outputting of the recommendation of that the implant should be cementless occurs when the relative motion is determined to be less than or equal to about 50 microns.

References in the specification to "one embodiment," "an embodiment," "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used in the description and claims, the singular form "a", "an" and "the" include both singular and plural references unless the context clearly dictates otherwise. For example, the term "strain gauge" may include, and is contemplated to include, a plurality of strain gauges. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

As used herein, the term "motion" or "micromotion" is intended to mean that the devices, systems, and methods include the recited elements, and may additionally include any other equivalent terms such as "displacement," or "micro displacement."

What is claimed is:

1. A system for detecting motion between an implant and a bone, the system comprising:
a bone locator configured to be coupled to the bone;

an implant attachment configured to be coupled to the implant, wherein:
the implant attachment comprises a detector, and
the implant attachment defines one or more apertures or surfaces for receiving a force from a force inducer,
wherein the detector includes a motion detector that is removably attached to the implant attachment and monitors the implant for movement between the bone and the implant when the implant is at rest and when the implant is under force; and
a data analyzer for determining the motion between the implant and the bone when the implant is at rest and when the implant is under force.

2. The system of claim 1, wherein the bone locator comprises a marking pin configured to reside in a drilled hole in the bone.

3. The system of claim 1, wherein the motion detector comprises a machine vision camera configured to generate a plurality of images showing a location of the bone locator.

4. The system of claim 1, wherein the data analyzer comprises:
a processor coupled to a memory and the motion detector, wherein the memory comprises computer-readable instructions stored thereon that, when executed by the processor, cause the processor to perform operations comprising:
receiving, from the motion detector, a first image of the bone locator coupled to the bone;
determining a first location of the bone locator in the first image of a field of view of the motion detector;
receiving, from a sensor removably coupled to the implant attachment and communicatively coupled to the processor, force signals indicative of forces the force induced on the implant being coupled to the bone;
receiving, from the motion detector, a second image of the bone locator coupled to the bone;
determining a second location of the bone locator in the second image of the field of view of the motion detector;
determining a relative motion between the implant and the bone based on a difference between the second location and the first location; and
outputting an indication of implant movement based on the determined relative motion.

5. The system of claim 4, wherein the determining the first location of the bone locator in the first image occurs when the implant is at rest.

6. The system of claim 4, wherein the determining the second location of the bone locator in the second image occurs when the implant is under the force.

7. The system of claim 4, wherein the instructions, when executed by the processor, further cause the processor to perform the operations comprising outputting a measurement of implant stability.

8. The system of claim 7, wherein the instructions, when executed by the processor, further cause the processor to perform the operations comprising outputting a recommendation of whether the implant should be cemented or cementless.

9. The system of claim 8, wherein the outputting of the recommendation that the implant should be cemented occurs when the relative motion is determined to be more than about 50 microns; and
wherein the outputting of the recommendation of that the implant should be cementless occurs when the relative motion is determined to be less than or equal to about 50 microns.

10. The system of claim 4, wherein the relative motion is determined to be either be more than about 50 microns or less than or equal to about 50 microns.

11. A computer-implemented method of measuring implant stability, the method comprising:

receiving, from a camera to recognize position of a bone locator in a field of view of the camera, a first image of the bone locator affixed to a bone, wherein the camera is removably attached to an implant;

determining a first location of the bone locator in the first image of the field of view of the camera;

receiving, from a sensor removably coupled to an implant attachment attached to the implant, force signals indicative of forces induced on an implant being coupled to the bone;

receiving, from the camera, a second image of the bone locator affixed to the bone;

determining a second location of the bone locator in the second image of the field of view of the camera;

determining a relative motion between the implant and the bone based on a difference between the second location when the implant is under force and the first location when the implant is at rest; and outputting an indication of the implant stability based on the determined relative motion of the motion between the implant and the bone.

12. The method of claim 11, further comprising outputting the measurement of the implant stability.

13. The method of claim 12, further comprising outputting a recommendation of whether the implant should be cemented or cementless.

14. The method of claim 13, wherein the outputting of the recommendation that the implant should be cemented occurs when the relative motion is determined to be more than about 50 microns; and wherein the outputting of the recommendation of that the implant should be cementless occurs when the relative motion is determined to be less than or equal to about 50 microns.

15. The method of claim 11, wherein the relative motion is determined to be either be more than about 50 microns or less than or equal to about 50 microns.

16. The method of claim 11, wherein the camera comprises a machine vision camera.

17. The method of claim 11, wherein the sensor comprises a strain gauge.

18. A non-transitory computer-readable medium comprising computer-readable instructions, wherein the computer-readable instructions, when executed by a processor, cause the processor to perform operations comprising:

receiving, from a machine vision camera, a first image of a bone locator affixed to a bone;

determining a first location of the bone locator in the first image of a field of view of the machine vision camera;

receiving, from a sensor removably coupled to an implant attachment attached to the implant, force signals indicative of forces induced on an implant being coupled to the bone, wherein the machine vision camera is removably attached to the implant attachment, and the implant attachment receives a force from a force inducer driving the forces on the implant;

receiving, from the machine vision camera, a second image of the bone locator affixed to the bone;

determining a second location of the bone locator in the second image of the field of view of the machine vision camera;

determining a relative motion between the implant and the bone based on a difference between the second location when the implant is under force and the first location when the implant is at rest; and outputting an indication of implant movement based on the determined relative motion.

19. The non-transitory computer-readable medium of claim 18, wherein the force inducer comprises the sensor.

20. The non-transitory computer-readable medium of claim 18, wherein the force inducer comprises a torque wrench.

* * * * *